US009714253B2

(12) United States Patent
Kitamura et al.

(10) Patent No.: US 9,714,253 B2
(45) Date of Patent: Jul. 25, 2017

(54) ORGANIC THIN FILM TRANSISTOR, ORGANIC SEMICONDUCTOR THIN FILM, AND ORGANIC SEMICONDUCTOR MATERIAL

(71) Applicant: FUJIFILM Corporation, Tokyo (JP)

(72) Inventors: Tetsu Kitamura, Ashigarakami-gun (JP); Koji Takaku, Ashigarakami-gun (JP); Wataru Sotoyama, Ashigarakami-gun (JP); Yuki Hirai, Ashigarakami-gun (JP); Masaru Kinoshita, Ashigarakami-gun (JP); Yuuta Shigenoi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/632,741

(22) Filed: Feb. 26, 2015

(65) Prior Publication Data

US 2015/0166561 A1     Jun. 18, 2015

Related U.S. Application Data

(63) Continuation of application No. PCT/JP2013/071322, filed on Aug. 7, 2013.

(30) Foreign Application Priority Data

Aug. 27, 2012 (JP) ................................. 2012-187058
Feb. 4, 2013 (JP) ................................. 2013-019584

(51) Int. Cl.
C07D 307/91 (2006.01)
H01L 51/00 (2006.01)
(Continued)

(52) U.S. Cl.
CPC .......... C07D 493/04 (2013.01); C07F 7/0812 (2013.01); C07F 7/0852 (2013.01);
(Continued)

(58) Field of Classification Search
CPC ........................... C07D 307/91; C07D 491/04
See application file for complete search history.

(56) References Cited

U.S. PATENT DOCUMENTS 8,057,919 B2   11/2011  Kato et al.
8,138,355 B2    3/2012  Watanabe
(Continued)

FOREIGN PATENT DOCUMENTS

JP    2007-088222 A    4/2007
JP    2008-081494 A    4/2008
(Continued)

OTHER PUBLICATIONS

Machine translated English language equivalent of JP 2010-045281 (Feb. 2010, 31 pages).*
(Continued)

*Primary Examiner* — Brieann R Fink
(74) *Attorney, Agent, or Firm* — Sughrue Mion, PLLC

(57) ABSTRACT

An organic thin film transistor having a semiconductor active layer containing a compound represented by the formula (1) has a high carrier mobility and a small change in the threshold voltage after repeated operation. $R^1$ to $R^{10}$ represent H or a substituent, provided that at least one of $R^1$ to $R^4$ and $R^6$ to $R^9$ represents a substituent represented by -L-R, L represents a specific divalent linking group, and
(Continued)

R represents an alkyl group, an oligooxyethylene group, an oligosiloxane group, or a trialkylsilyl group.

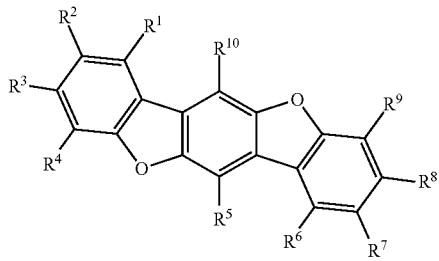

(1)

11 Claims, 1 Drawing Sheet

(51) Int. Cl.
C07D 493/04 (2006.01)
C07F 7/08 (2006.01)
H01L 51/05 (2006.01)

(52) U.S. Cl.
CPC ...... H01L 51/0062 (2013.01); H01L 51/0065 (2013.01); H01L 51/0073 (2013.01); H01L 51/0545 (2013.01); H01L 51/0558 (2013.01)

(56) References Cited

U.S. PATENT DOCUMENTS

| | | | |
|---|---|---|---|
| 8,372,529 B2 | 2/2013 | Kato et al. | |
| 8,409,730 B2 | 4/2013 | Kato et al. | |
| 8,852,756 B2 | 10/2014 | Vestweber et al. | |
| 2006/0125009 A1 | 6/2006 | Wu et al. | |
| 2006/0128969 A1 | 6/2006 | Li et al. | |
| 2008/0191199 A1* | 8/2008 | Anemian | C07C 15/28 257/40 |
| 2008/0220285 A1 | 9/2008 | Vestweber et al. | |
| 2009/0261300 A1* | 10/2009 | Watanabe | C07C 17/12 252/500 |
| 2009/0302743 A1 | 12/2009 | Kato et al. | |
| 2011/0272684 A1* | 11/2011 | Parham | C07D 209/94 257/40 |
| 2012/0074396 A1 | 3/2012 | Meng et al. | |
| 2012/0085995 A1 | 4/2012 | Kato et al. | |
| 2012/0112629 A1 | 5/2012 | Kato et al. | |
| 2013/0153874 A1 | 6/2013 | Kato et al. | |
| 2015/0031896 A1 | 1/2015 | Vestweber et al. | |

FOREIGN PATENT DOCUMENTS

| | | | |
|---|---|---|---|
| JP | 2008-147256 A | | 6/2008 |
| JP | 2009-519595 A | | 5/2009 |
| JP | 2010-045281 A | | 2/2010 |
| JP | 2010045281 A | * | 2/2010 |
| JP | 2010-229048 A | | 10/2010 |
| JP | 2012-515733 A | | 7/2012 |
| TW | 201038576 A1 | | 11/2010 |
| WO | 2006/122630 A1 | | 11/2006 |
| WO | 2007/068618 A1 | | 6/2007 |
| WO | 2009/148016 A1 | | 12/2009 |

OTHER PUBLICATIONS

Wirth (Synthesis and properties of oxido-p-oligophenylenes. XVIII. Poly- and oligophenylenes. Macromol. Chem. 1965, 86, pp. 139-167).*
International Preliminary Report on Patentability dated Mar. 12, 2015, issued by the International Bureau in corresponding International Application No. PCT/JP2013/071322.
English excerpt of Molecular Electronics and Bioelectronics, The Japan Society of Applied Physics, vol. 22, pp. 9-12 (2011).
Office Action dated Jul. 14, 2015, issued by the Japanese Patent Office in counterpart Japanese Application No. 2013-019584.
Molecular Electronics and Bioelectronics, The Japan Society of Applied Physics, 2011, pp. 9-12, vol. 22, No. 1.
Kazuo Takimiya, et al., "Thienoacene-Based Organic Semiconductors", Advanced Materials, 2011, pp. 4347-4370, vol. 23.
International Search Report for PCT/JP2013/071322 dated Oct. 22, 2013 [PCT/ISA/210].
Written Opinion for PCT/JP2013/071322 dated Oct. 22, 2013 [PCT/ISA/237].
Office Action dated Feb. 15, 2016 from the Korean Intellectual Property Office issued in corresponding Korean Application No. 10-2015-7007353.
Office Action dated Jul. 29, 2016 from the Korean Intellectual Property Office in counterpart Korean Application No. 2015-7007353.
Office Action dated Sep. 29, 2016 from the Korean Intellectual Property Office in counterpart Korean Application No. 10-2015-7007353.
Office Action dated Sep. 26, 2016 from the Taiwanese Intellectual Property Office in counterpart Taiwanese Application No. 102129074.
Office Action dated Mar. 24, 2017 from the Korean Intellectual Property Office in counterpart Korean Application No. 10-2015-7007353.

* cited by examiner

ORGANIC THIN FILM TRANSISTOR, ORGANIC SEMICONDUCTOR THIN FILM, AND ORGANIC SEMICONDUCTOR MATERIAL

CROSS-REFERENCE TO RELATED APPLICATIONS

This application is a Continuation of PCT International Application No. PCT/JP2013/071322, filed Aug. 7, 2013, which claims priority under 35 U.S.C. Section 119(a) to Japanese Patent Application No. 2012-187058 filed on Aug. 27, 2012 and Japanese Patent Application No. 2013-019584 filed on Feb. 4, 2013. Each of the above applications is hereby expressly incorporated by reference, in its entirety, into the present application.

BACKGROUND OF THE INVENTION

Field of the Invention

The present invention relates to an organic thin film transistor, an organic semiconductor thin film, and an organic semiconductor material. Specifically, the invention relates to an organic semiconductor material for a non-light-emitting organic semiconductor device containing a compound having a benzobisbenzofuran (which may be hereinafter referred to as BBBF) structure, an organic semiconductor thin film containing the material, and an organic thin film transistor using the thin film.

Background Art

A device using an organic semiconductor material is expected to have various advantages as compared to a device using an ordinary inorganic semiconductor material, such as silicon, and thus is receiving a high level of interest. Examples of the device using an organic semiconductor material include a photoelectric conversion device using an organic semiconductor material as a photoelectric conversion material, such as an organic thin film solar cell and a solid-state imaging device, and a non-light-emitting organic transistor. A device using an organic semiconductor material has a possibility of producing a large area device at a low temperature and low cost, as compared to a device using an inorganic semiconductor material. Furthermore, the material characteristics may be easily changed by changing the molecular structure thereof, thereby providing a wide range of varieties of the materials, and thus functions and devices that are not achieved with an inorganic semiconductor material may be realized.

For example, Patent Reference 1 describes the compound represented by the following general formula having a condensed ring containing five rings including aromatic heterocyclic rings as a partial structure (in which ring A and ring B each represent a benzene ring or a particular 5-membered aromatic heterocyclic ring; $T^1$ and $T^2$ each represent sulfur, selenium, tellurium, oxygen, phosphorus, boron or aluminum; $R^1$ to $R^4$ each represent a hydrogen atom, an alkyl group, or the like; and l and m each represent 0 or 1). Patent Reference 1 describes that the compound represented by the following general formula may form a semiconductor active layer and may be an organic semiconductor material that is capable of forming the film by coating. In the literature, the compound is used as an organic semiconductor material and forms an organic thin film, but the transistor characteristics and the like thereof are not described.

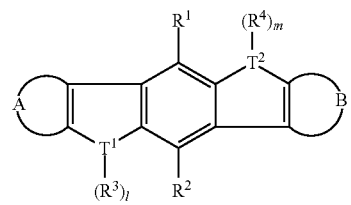

Patent Reference 2 describes an example of the application as an organic EL device of a condensed ring compound containing an aromatic heterocyclic ring that is defined in structural characteristics from the other view point than the aforementioned general formula. However, Patent Reference 2 fails to describe examples of an application as an organic transistor and transistor characteristics.

Non-patent Reference 1 and Patent References 3 to 6 describe the use of a polycyclic condensed ring compound containing an aromatic heterocyclic ring as an organic transistor. Non-patent Reference 1 suggests that some of compounds having a BBBF skeleton appear promising as a material for an organic thin film transistor. However, the organic thin film transistor only has transistor characteristics that are in an elementary level and fails to achieve a practical level due to the low mobility. Patent References 3 to 6 describe the usefulness of a compound having a BBBF skeleton in an organic semiconductor device, but only the limited compounds are shown to have the usefulness as an organic semiconductor material for an organic thin film transistor.

CITATION LIST

Patent References

Patent Reference 1: JP-A-2008-81494
Patent Reference 2: JP-A-2010-45281
Patent Reference 3: JP-A-2007-88222
Patent Reference 4: JP-A-2009-519595
Patent Reference 5: WO 2006/122630
Patent Reference 6: JP-A-2008-147256

Non-Patent Reference

Non-patent Reference 1: Molecular Electronics and Bioelectronics, The Japan Society of Applied Physics, vol. 22, pp. 9-12 (2011)

SUMMARY OF INVENTION

As described in Patent Reference 2, the usefulness as an organic EL device material of a polycyclic condensed ring compound containing an aromatic heterocyclic ring, such as a BBBF skeleton, has been known. However, it may not be said that a compound that is useful as an organic EL device material is immediately useful as a semiconductor material for an organic thin film transistor. This is because the characteristics demanded for the organic compound are different between an organic EL device and an organic thin film transistor. Specifically, an organic thin film transistor requires charge transport in a long distance (generally from several micrometers to several hundred micrometers) between electrodes in the thin film in-plane direction, which is different from the case of an organic EL device and the like, which require charge transport in a distance (generally from several nanometers to several hundred nanometers) in the film thickness direction, and thus demands a remarkably high carrier mobility. Accordingly, an organic compound that has high crystallinity is demanded as the semiconductor material for an organic thin film transistor. On the other hand, a device that has a high light emission efficiency and achieves uniform in-plane light emission is demanded as the organic EL device. In general, an organic compound having high crystallinity may cause light emission defects, such as in-plane unevenness in electric field intensity, in-plane unevenness in light emission, and light emission quenching, and therefore the organic EL device material may not be enhanced in crystallinity. Accordingly, even when an organic compound that constitutes an organic EL device is diverted as it is to an organic semiconductor material, good transistor characteristics may not be obtained.

As a result of practical application by the present inventors of the compounds that are applied to an organic thin film transistor in the aforementioned Patent References to an organic thin film transistor, a problem has been found that sufficient transistor characteristics are not obtained. Specifically, it has been found as a result of investigations made by the inventors that in the case where the compounds, the structures of which are specifically described in the Patent References, are applied as an organic semiconductor material to an organic thin film transistor, a high carrier mobility is not obtained. Furthermore, it has been found as a result of investigations made by the inventors that in the case where the compounds are applied as an organic semiconductor material to an organic thin film transistor, which is then operated repeatedly, the change in the threshold voltage is increased. The increase of the threshold voltage brings about such problems as deterioration in reliability of the transistor, and failure of long-term use of the semiconductor.

Under the circumstances, the inventors have made investigations for providing an organic thin film transistor showing good transistor characteristics for solving the aforementioned problems. Specifically, an object to be achieved by the inventors is to provide a semiconductor material that has a high carrier mobility and a small change in the threshold voltage after repeated operation, and to provide an organic thin film transistor that has good transistor characteristics by applying the semiconductor material thereto.

As a result of earnest investigations made by the inventors for solving the problem, it has been found that a BBBF derivative having a particular structure has high crystallinity and provides an organic thin film advantageous to carrier transport. Accordingly, the inventors have succeeded to provide an organic thin film transistor that has a high carrier mobility, and thus the invention has been completed.

The inventors have also found that the organic thin film transistor obtained in the invention has a small change in the threshold voltage after repeated operation, and have succeeded to provide an organic thin film transistor that is capable of being used stably for a prolonged period of time.

Specifically, the invention includes the following aspects.

(1) An organic thin film transistor having a semiconductor active layer containing a compound represented by the following general formula (1):

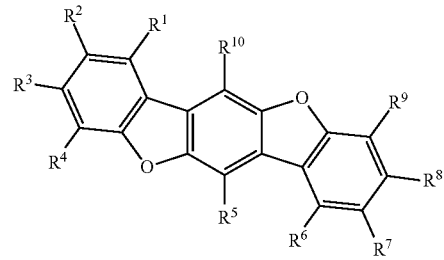

General Formula (1)

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R     General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

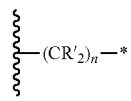

(L-1)

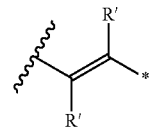

(L-2)

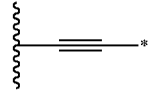

(L-3)

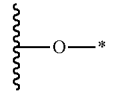

(L-4)

(L-5)

(L-6)
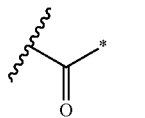

(L-7)
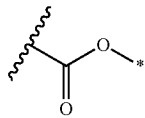

(L-8)
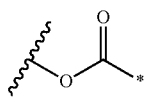

(L-9)
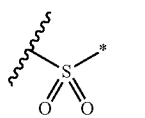

(L-10)
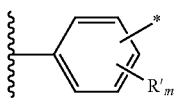

(L-11)
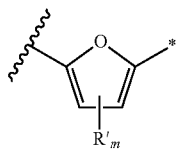

(L-12)
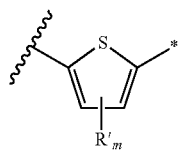

(L-13)
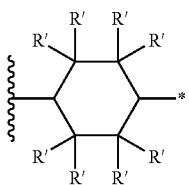

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

(2) In the organic thin film transistor according to the item (1), it is preferred that the compound represented by the general formula (1) is a compound represented by the following general formula (1A):

General Formula (1A)
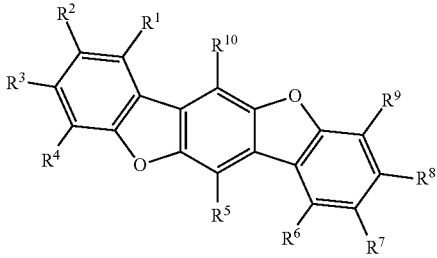

wherein in the general formula (1A), $R^1$ to $R^{10}$ each independently represent a hydrogen atom or a substituent, provided that at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R    General Formula (W)

wherein in the general formula (W), L represents a divalent linking group represented by one of the general formulae (L-1) to (L-12) or a divalent linking group containing two or more of divalent linking groups represented by any of the general formulae (L-1) to (L-12) bonded to each other; and R represents a substituted or unsubstituted alkyl group having 2 or more carbon atoms, an oligooxyethylene group having a number of repetition of oxyethylene units of 2 or more, or an oligosiloxane group having 2 or more silicon atoms.

(3) In the organic thin film transistor according to the item (1), it is preferred that the compound represented by the general formula (1) is a compound represented by one of the following general formulae (2-1), (2-2), (2-3) and (2-4):

General Formula (2-1)
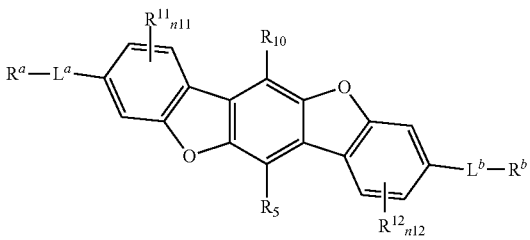

wherein in the general formula (2-1), $L^a$ and $L^b$ each independently represent a divalent linking group represented by one of the following general formulae (L-1) to (L-13) or a divalent linking group containing two or more of divalent linking groups represented by any of the following general formulae (L-1) to (L-13) bonded to each other; $R^a$ and $R^b$ each independently represent a substituted or unsubstituted alkyl group having 2 or more carbon atoms, an oligooxyethylene group having a number of repetition of oxyethylene units of 2 or more, an oligosiloxane group having a number of repetition of siloxane units of 2 or more, or a substituted or unsubstituted trialkylsilyl group, provided that $R^a$ and $R^b$ each are capable of representing a substituted or unsubstituted trialkylsilyl group only in the case where $L^a$ or $L^b$ adjacent to $R^a$ or $R^b$ represents a divalent linking group represented by the following general formula (L-3); $R^{11}$ and $R^{12}$ each independently represent a substituent; and n11 and n12 each independently represent an integer of from 0 to 3, General Formula (2-2)

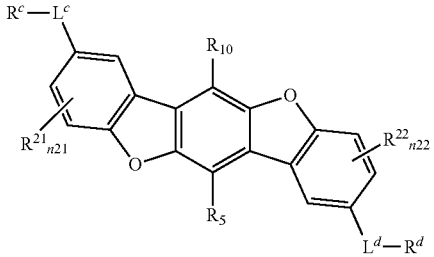

wherein in the general formula (2-2), $L^c$ and $L^d$ each independently represent a divalent linking group represented by one of the following general formulae (L-1) to (L-13) or a divalent linking group containing two or more of divalent linking groups represented by any of the following general formulae (L-1) to (L-13) bonded to each other; $R^c$ and $R^d$ each independently represent a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^c$ and $R^d$ each are capable of representing a substituted or unsubstituted trialkylsilyl group only in the case where $L^c$ or $L^d$ adjacent to $R^c$ or $R^d$ represents a divalent linking group represented by the following general formula (L-3); $R^{21}$ and $R^{22}$ each independently represent a substituent (provided that $R^{21}$ and $R^{22}$ are not a group represented by the general formula (W)); and n21 and n22 each independently represent an integer of from 0 to 3, General Formula (2-3)

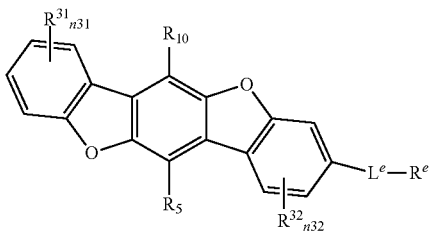

wherein in the general formula (2-3), $L^e$ represents a divalent linking group represented by one of the following general formulae (L-2) to (L-13) or a divalent linking group containing two or more of divalent linking groups represented by any of the following general formulae (L-1) to (L-13) bonded to each other (provided that $L^e$ is not a divalent linking group that contains only two or more of divalent linking groups represented by the general formula (L-1) bonded to each other); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^e$ is capable of representing a substituted or unsubstituted trialkylsilyl group only in the case where $L^e$ adjacent to $R^e$ represents a divalent linking group represented by the following general formula (L-3); $R^{31}$ and $R^{32}$ each independently represent a substituent (provided that $R^{31}$ is not a group represented by the general formula (W)); n31 represents an integer of from 0 to 4; and n32 represents an integer of from 0 to 3, General Formula (2-4)

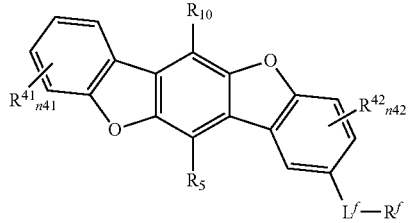

wherein in the general formula (2-4), $L^f$ represents a divalent linking group represented by one of the following general formulae (L-2) to (L-13) or a divalent linking group containing two or more of divalent linking groups represented by any of the following general formulae (L-1) to (L-13) bonded to each other (provided that $L^f$ is not a divalent linking group that contains only two or more of divalent linking groups represented by the general formula (L-1) bonded to each other); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^f$ is capable of representing a substituted or unsubstituted trialkylsilyl group only in the case where $L^f$ adjacent to $R^f$ represents a divalent linking group represented by the following general formula (L-3); $R^{41}$ and $R^{42}$ each independently represent a substituent (provided that $R^{41}$ and $R^{42}$ are not a group represented by the general formula (W)); n41 represents an integer of from 0 to 4; and n42 represents an integer of from 0 to 3:

(L-1)
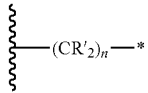

(L-2)
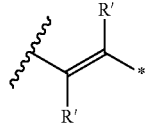

(L-3)
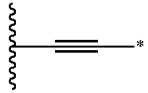

(L-4)
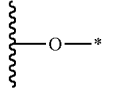

(L-5)
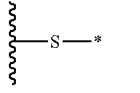

-continued

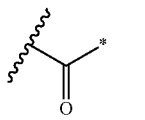 (L-6)

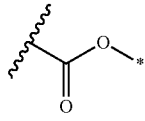 (L-7)

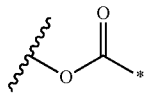 (L-8)

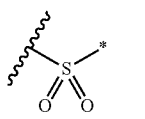 (L-9)

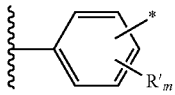 (L-10)

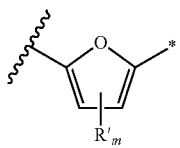 (L-11)

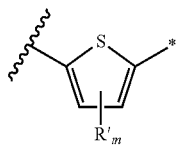 (L-12)

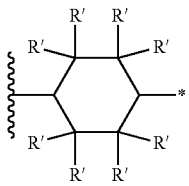 (L-13)

wherein in the general formulae (L-1) to (L-13) in the general formulae (2-1) to (2-4), a position shown by a wave line represents a bonding position to the benzobisbenzofuran skeleton; a position shown by * each independently represent the bonding position to one of $R^a$, $R^b$, $R^c$, $R^d$, $R^e$ and $R^f$ adjacent to the general formulae (L-1) to (L-13); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

(4) In the organic thin film transistor according to the item (3), it is preferred that in the general formula (2-1) or (2-2), $L^a$, $L^b$, $L^c$ and $L^d$ each independently represent a divalent linking group represented by the general formula (L-1), (L-3), (L-4), (L-5) or (L-13) or a divalent linking group containing two or more of the divalent linking groups bonded to each other.

(5) In the organic thin film transistor according to the item (3), it is preferred that in the general formula (2-3) or (2-4), $L^e$ and $L^f$ each independently represent a divalent linking group represented by the general formula (L-3), (L-4), (L-5) or (L-13) or a divalent linking group containing two or more of the divalent linking groups bonded to each other.

(6) In the organic thin film transistor according to any one of the items (3) to (5), it is preferred that in the general formula (2-1), (2-2), (2-3) or (2-4), all $R^a$, $R^b$, $R^c$, $R^d$, $R^e$ and $R^f$ each independently represent an alkyl group.

(7) In the organic thin film transistor according to any one of the items (3) to (5), it is preferred that in the general formula (2-1), (2-2), (2-3) or (2-4), all $R^a$ and $R^b$ each independently represent an alkyl group having from 2 to 12 carbon atoms; $R^c$ and $R^d$ each independently represent an alkyl group having from 2 to 7 carbon atoms; $R^e$ represents an alkyl group having from 2 to 12 carbon atoms; and $R^f$ represents an alkyl group having from 2 to 12 carbon atoms.

(8) A compound represented by one of the following general formulae (2-1'), (2-2'), (2-3') and (2-4'):

General Formula (2-1')

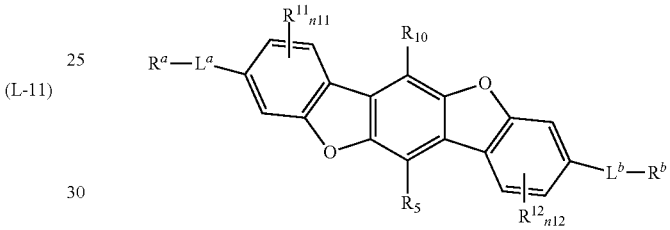

wherein in the general formula (2-1'), $L^a$ and $L^b$ each independently represent a divalent linking group represented by one of the following general formulae (L-1) to (L-13) or a divalent linking group containing two or more of divalent linking groups represented by any of the following general formulae (L-1) to (L-13) bonded to each other; $R^a$ and $R^b$ each independently represent a substituted or unsubstituted alkyl group having from 2 to 12 carbon atoms, an oligooxyethylene group having a number of repetition of oxyethylene units of 2 or more, an oligosiloxane group having a number of repetition of siloxane units of 2 or more, or a substituted or unsubstituted trialkylsilyl group, provided that $R^a$ and $R^b$ each are capable of representing a substituted or unsubstituted trialkylsilyl group only in the case where $L^a$ or $L^b$ adjacent to $R^a$ or $R^b$ represents a divalent linking group represented by the following general formula (L-3); $R^{11}$ and $R^{12}$ each independently represent a substituent; and n11 and n12 each independently represent an integer of from 0 to 3, General Formula (2-2')

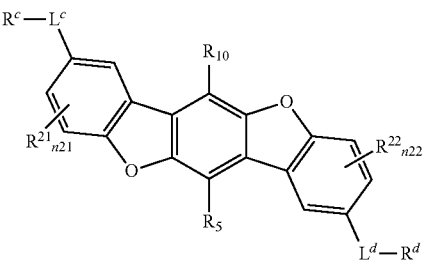

wherein in the general formula (2-2'), $L^c$ and $L^d$ each independently represent a divalent linking group represented by one of the following general formulae (L-1) to (L-13) or a divalent linking group containing two or more of divalent linking groups represented by any of the following general formulae (L-1) to (L-13) bonded to each other; $R^c$ and $R^d$ each independently represent a substituted or unsubstituted alkyl group having from 2 to 7 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^c$ and $R^d$ each are capable of representing a substituted or unsubstituted trialkylsilyl group only in the case where $L^c$ or $L^d$ adjacent to $R^c$ or $R^d$ represents a divalent linking group represented by the following general formula (L-3); $R^{21}$ and $R^{22}$ each independently represent a substituent (provided that $R^{21}$ and $R^{22}$ are not a group represented by the general formula (W)); and n21 and n22 each independently represent an integer of from 0 to 3, General Formula (2-3')

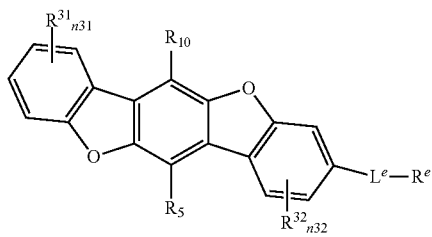

wherein in the general formula (2-3'), $L^e$ represents a divalent linking group represented by one of the following general formulae (L-2) to (L-13) or a divalent linking group containing two or more of divalent linking groups represented by any of the following general formulae (L-1) to (L-13) bonded to each other (provided that $L^e$ is not a divalent linking group that contains only two or more of divalent linking groups represented by the general formula (L-1) bonded to each other); $R^e$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^e$ is capable of representing a substituted or unsubstituted trialkylsilyl group only in the case where $L^e$ adjacent to $R^e$ represents a divalent linking group represented by the following general formula (L-3); $R^{31}$ and $R^{32}$ each independently represent a substituent (provided that $R^{31}$ is not a group represented by the general formula (W)); n31 represents an integer of from 0 to 4; and n32 represents an integer of from 0 to 3, General Formula (2-4')

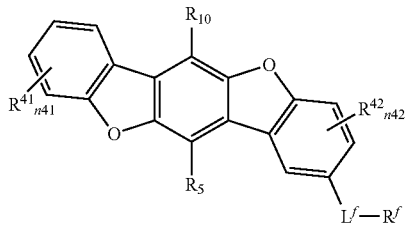

wherein in the general formula (2-4'), $L^f$ represents a divalent linking group represented by one of the following general formulae (L-2) to (L-13) or a divalent linking group containing two or more of divalent linking groups represented by any of the following general formulae (L-1) to (L-13) bonded to each other (provided that $L^f$ is not a divalent linking group that contains only two or more of divalent linking groups represented by the general formula (L-1) bonded to each other); $R^f$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^f$ is capable of representing a substituted or unsubstituted trialkylsilyl group only in the case where $L^f$ adjacent to $R^f$ represents a divalent linking group represented by the following general formula (L-3); $R^{41}$ and $R^{42}$ each independently represent a substituent (provided that $R^{41}$ and $R^{42}$ are not a group represented by the general formula (W)); n41 represents an integer of from 0 to 4; and n42 represents an integer of from 0 to 3:

(L-1)

(L-2)

(L-3)

(L-4)

(L-5)

(L-6)

(L-7)

(L-8)

(L-9)

-continued

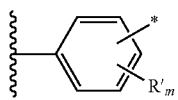 (L-10)

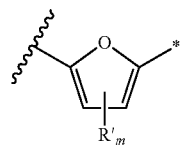 (L-11)

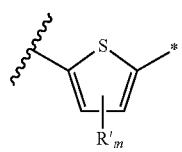 (L-12)

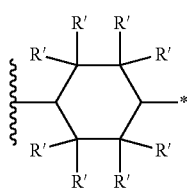 (L-13)

wherein in the general formulae (L-1) to (L-13) in the general formulae (2-1') to (2-4'), a position shown by a wave line represents a bonding position to the benzobisbenzofuran skeleton; a position shown by * each independently represent the bonding position to one of $R^a$, $R^b$, $R^c$, $R^d$, $R^e$ and $R^f$ adjacent to the general formulae (L-1) to (L-13); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

(9) An organic semiconductor material for a non-light-emitting organic semiconductor device, containing a compound represented by the general formula (1) according to the item (1).

(10) A material for an organic thin film transistor, containing a compound represented by the general formula (1) according to the item (1).

(11) A coating solution for a non-light-emitting organic semiconductor device, containing a compound represented by the general formula (1) according to the item (1).

(12) A coating solution for a non-light-emitting organic semiconductor device, containing a compound represented by the general formula (1) according to the item (1) and a polymer binder.

(13) An organic semiconductor thin film containing a compound represented by the general formula (1) according to the item (1).

(14) An organic semiconductor thin film containing a compound represented by the general formula (1) according to the item (1) and a polymer binder.

(15) In the organic semiconductor thin film according to the item (13) or (14), it is preferred that the organic semiconductor thin film is produced by a solution coating method.

According to the invention, a semiconductor material that has high crystallinity and forms an organic thin film advantageous for carrier transport may be provided, and thereby an organic thin film transistor that has a high carrier mobility may be provided.

According to the invention, furthermore, an organic thin film transistor that has a small change in the threshold voltage after repeated operation may be provided, and thereby the organic thin film of the organic thin film transistor may have high chemical stability, a high film density, and the like, and may be capable of functioning as a transistor for a prolonged period of time.

DESCRIPTION OF EMBODIMENTS

Figure 1:
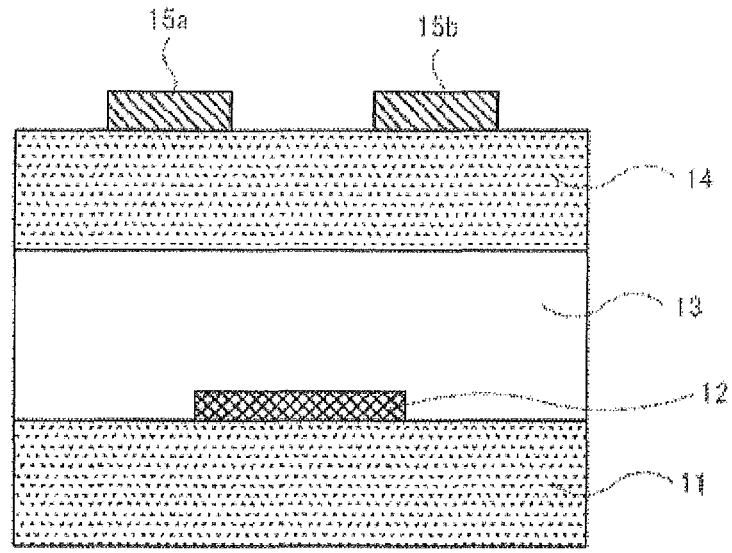
FIG. 1 is a schematic illustration showing an example of a cross section of a structure of an organic thin film transistor device according to the invention.

The invention will be described in detail below. The following description of constitutional elements may be made based on representative embodiments and specific examples, but the invention is not limited to the embodiments and examples. In this specification, numeric ranges expressed using "to" means a numeric range involving the numerals recited before and after "to" as the lower limit and the upper limit.

In the invention, the hydrogen atoms that are referred for the description of the general formulae herein include isotopes thereof (such as a deuterium atom) unless otherwise indicated. The atoms constituting the substituents also include isotopes thereof.

Organic Thin Film Transistor

The organic thin film transistor of the invention has a semiconductor active layer, and the semiconductor active layer contains a compound represented by the following general formula (1).

Benzobisbenzofuran Derivative

One of the features of the invention is that the semiconductor active layer contains a compound represented by the following general formula (1):

General Formula (1)

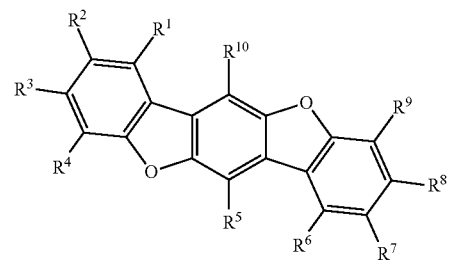

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other.

-L-R  General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

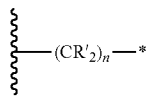
(L-1)

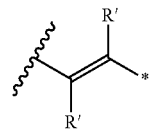
(L-2)

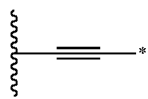
(L-3)

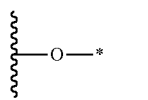
(L-4)

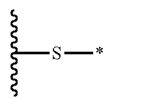
(L-5)

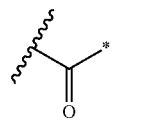
(L-6)

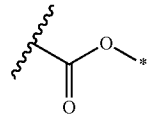
(L-7)

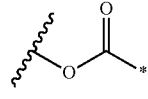
(L-8)

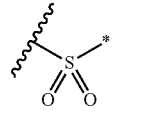
(L-9)

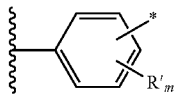
(L-10)

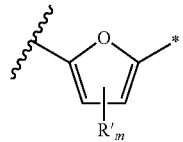
(L-11)

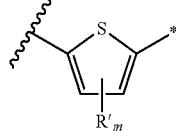
(L-12)

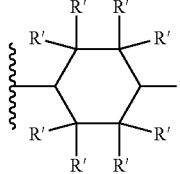
(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

The compound represented by the general formula (1) may have favorable capability as an organic semiconductor material even after storing under a high temperature and high humidity condition. For example, even after storing under a high temperature and high humidity condition, a high carrier mobility may be obtained, and the change in the mobility may be small. According to the capability, the organic thin film transistor of the invention may effectively function as a transistor under severe condition.

In the invention, furthermore, the change in the threshold voltage after repeated operation may be small, and thereby the organic thin film transistor of the invention may exhibit good transistor characteristics for a prolonged period of time.

In the invention, moreover, the compound represented by the general formula (1) has the aforementioned structure and thus may provide an organic thin film having good film quality. The compound represented by the general formula (1) may have good crystallinity and thus may provide a sufficient film thickness, and the resulting film may have good quality. In the invention, a high carrier mobility may be obtained due to the good crystallinity, thereby providing excellent transistor characteristics.

The compound represented by the general formula (1) is preferably represented by one of the following general formulae (2-1), (2-2), (2-3) and (2-4), and is also preferably a compound represented by the following general formula (1A).

General Formula (1A)

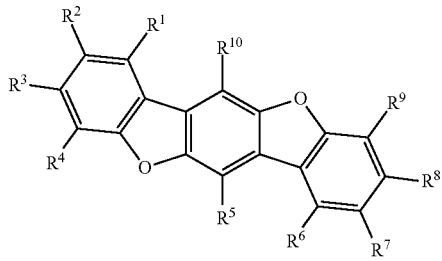

wherein in the general formula (1A), $R^1$ to $R^{10}$ each independently represent a hydrogen atom or a substituent, provided that at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R                  General Formula (W)

wherein in the general formula (W) contained in the general formula (1A), L represents a divalent linking group represented by one of the general formulae (L-1) to (L-12) or a divalent linking group containing two or more of divalent linking groups represented by any of the general formulae (L-1) to (L-12) bonded to each other; and R represents a substituted or unsubstituted alkyl group having 2 or more carbon atoms, an oligooxyethylene group having a number of repetition of oxyethylene units of 2 or more, or an oligosiloxane group having 2 or more silicon atoms.

In the general formula (1), $R^1$ to $R^{10}$ each independently represent a hydrogen atom or a substituent. At least one of $R^1$ to $R^4$ and $R^6$ to $R^9$ represents a substituent represented by the following general formula (W), provided that in the general formula (W), when L represents a divalent linking group represented solely by the following general formula (L-1), at least two of $R^1$ to $R^4$ and $R^6$ to $R^9$ each represent a substituent represented by the following general formula (W). The substituents represented by $R^1$ to $R^4$ and $R^6$ to $R^9$ do not form a condensed ring by being bonded to each other.

The compound represented by the general formula (1) has $R^1$ to $R^{10}$, at least one of which represents a substituent represented by the following general formula (W), and thereby the material may have good solution process suitability and good molecular arrangement in the film. Accordingly, the compound may enhance the production efficiency of the organic thin film capable of being applied to an organic thin film transistor, and may reduce the production cost. The compound may also enhance the carrier transport characteristics, such as the carrier mobility, and the chemical and physical stability of the thin film.

In the general formula (W) in the general formula (1), L represents a divalent linking group represented by one of the general formulae (L-1) to (L-13) or a divalent linking group containing two or more of divalent linking groups represented by any of the general formulae (L-1) to (L-13) bonded to each other, and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the general formula (L-3).

In the case where the number of the substituents represented by the general formula (W) contained in the compound represented by the general formula (1) is 2 or more, R in the general formula (W) preferably represents a substituted or unsubstituted alkyl group having 2 or more carbon atoms or a substituted or unsubstituted trialkylsilyl group from the standpoint of suppressing the change in the mobility after storing under a high temperature and high humidity condition.

In the case where the number of the substituent represented by the general formula (W) contained in the compound represented by the general formula (1) is 1, R in the general formula (W) preferably represents a substituted or unsubstituted alkyl group having 2 or more carbon atoms, an oligosiloxane group having 2 or more silicon atoms, or a substituted or unsubstituted trialkylsilyl group, and more preferably a substituted or unsubstituted alkyl group having 2 or more carbon atoms or a substituted or unsubstituted trialkylsilyl group.

In the case where R in the general formula (W) represents an alkyl group, the number of carbon atoms thereof is preferably from 2 to 18, more preferably from 2 to 12, further preferably from 2 to 10, and still further preferably from 2 to 7. The alkyl group preferably has from 2 to 7 carbon atoms since the solubility of the compound in a solvent may be enhanced as compared to the case of a number of carbon atoms of 8 or more. The alkyl group capable of being R may be any of linear, branched and cyclic, and a substituted or unsubstituted alkyl group may be used therefor. In the case where R has a substituent, examples of the substituent include a halogen atom, and preferably a fluorine atom. In the case where R represents an alkyl group having a fluorine atom, a perfluoroalkyl group may be formed by replacing all the hydrogen atoms of the alkyl group with fluorine atoms.

In the case where R in the general formula (W) represents an oligooxyethylene group having a number of repetition of oxyethylene units of 2 or more, the oligooxyethylene group represented by R herein means a group represented by —$(CH_2CH_2)_xOY$ (wherein the number of repetition of oxyethylene units x represents an integer of 2 or more, and the end group Y represents a hydrogen atom or a substituent). In the case where the end group Y of the oligooxyethylene group is a hydrogen atom, the group is a hydroxyl group. The number of repetition of oxyethylene units x is preferably from 2 to 4, and more preferably from 2 to 3. The end hydroxyl group of the oligooxyethylene group is preferably sealed, i.e., Y preferably represents a substituent. In this case, the hydroxyl group is preferably sealed with an alkyl group having from 1 to 3 carbon atoms, i.e., Y preferably represents an alkyl group having from 1 to 3 carbon atoms. The hydroxyl group is preferably sealed, for example, with a methyl group or an ethyl group, and Y more preferably represents a methyl group or an ethyl group.

In the case where R in the general formula (W) represents an oligosiloxane group having 2 or more silicon atoms, the number of repetition of siloxane units is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, the Si atom is preferably bonded to a methyl group or an ethyl group. The Si atom may be bonded to the same alkyl groups or may be bonded to different alkyl groups or a hydrogen atom. All the siloxane units constituting the oligosiloxane group may be the same as each other or may be different from each other, and preferably are the same as each other.

Only in the case where L adjacent to R represents a divalent linking group represented by the general formula (L-3), R in the general formula (W) may represent a substituted or unsubstituted trialkylsilyl group. In the case where R in the general formula (W) represents a substituted or unsubstituted trialkylsilyl group, the number of carbon atoms of the alkyl group bonded to the Si atom is preferably from 1 to 3, and for example, a methyl group, an ethyl group or an isopropyl group is preferably bonded thereto. The Si atom may be bonded to the same alkyl groups or may be bonded to different alkyl groups. In the case where R represents a substituted trialkylsilyl group, the substituent is not particularly limited.

L represents a divalent linking group represented by one of the following general formulae (L-1) to (L-13) or a divalent linking group containing two or more of divalent linking groups represented by any of the following general formulae (L-1) to (L-13) bonded to each other:

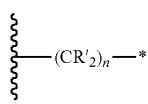
(L-1)

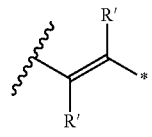
(L-2)

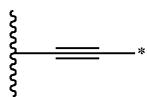
(L-3)

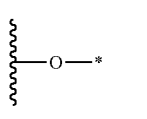
(L-4)

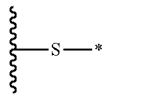
(L-5)

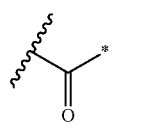
(L-6)

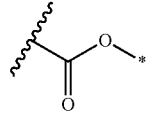
(L-7)

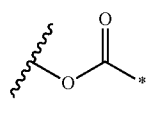
(L-8)

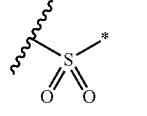
(L-9)

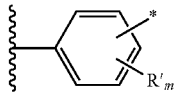
(L-10)

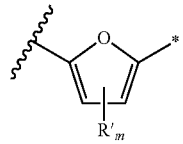
(L-11)

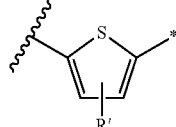
(L-12)

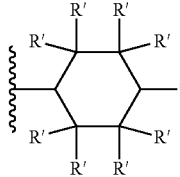
(L-13)

In the general formulae (L-1) to (L-13), a position shown by a wave line represents a bonding position to the BBBF skeleton; a position shown by * represents the bonding position to R in the general formula (W), provided that in the general formulae (L-1) to (L-13), a linking group represented by one of the general formulae (L-1) to (L-13) may be further inserted between the position shown by * and R in the general formula (W). In the case where L represents a linking group containing two or more of divalent linking groups represented by any of the following general formulae (L-1) to (L-13) bonded to each other, the number of the divalent linking groups represented by any of the following general formulae (L-1) to (L-13) bonded to each other is preferably from 2 to 4, and more preferably from 2 to 3. In the general formulae (L-10) to (L-13), in particular, it is also preferred that a linking group represented by one of the following general formulae (L-1) to (L-13) is further inserted between the position shown by * and R, and thereby L forms a linking group containing two or more of divalent linking groups represented by any of the following general formulae (L-1) to (L-13) bonded to each other.

In the general formula (L-1), n represents an integer of 1 or more, preferably an integer of from 1 to 10, more preferably an integer of from 1 to 6, and further preferably an integer of from 1 to 3.

In the general formulae (L-1), (L-2), (L-10), (L-11), (L-12) and (L-13), R' represents a hydrogen atom or a substituent.

Examples of the substituent R' in the general formulae (L-1), (L-2), (L-10), (L-11), (L-12) and (L-13) include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boric acid group (—B(OH)$_2$), a phosphato group (—OPO(OH)$_2$), a sulfato group (—OSO$_3$H), and other known substituents.

In the general formula (L-10), m represents 4. In the general formulae (L-11) and (L-12), m represents 2.

In the case where the number of the substituents represented by the general formula (W) contained in the compound represented by the general formula (1) is 2 or more, L in the general formula (W) preferably represents a divalent linking group represented by any of the general formulae (L-1), (L-3), (L-4), (L-5), (L-6), (L-10), (L-11), (L-12) and (L-13) or a divalent linking groups containing two or more of the divalent linking groups, more preferably a divalent linking group represented by any of the general formulae (L-1), (L-3), (L-4), (L-5), (L-10), (L-12) and (L-13) or a divalent linking groups containing two or more of the divalent linking groups, and particularly preferably a divalent linking group represented by any of the general formulae (L-1), (L-3), (L-4), (L-5) and (L-13) or a divalent linking groups containing two or more of the divalent linking groups.

In the case where the number of the substituent represented by the general formula (W) contained in the compound represented by the general formula (1) is 1, L in the general formula (W) preferably represents a divalent linking group represented by any of the general formulae (L-1), (L-3), (L-4), (L-5), (L-6), (L-10), (L-11), (L-12) and (L-13) or a divalent linking groups containing two or more of the divalent linking groups, more preferably a divalent linking group represented by any of the general formulae (L-1), (L-3), (L-4), (L-5), (L-10), (L-12) and (L-13) or a divalent linking groups containing two or more of the divalent linking groups, particularly preferably a divalent linking group represented by any of the general formulae (L-3), (L-4), (L-5) and (L-13) or a divalent linking groups containing two or more of the divalent linking groups, and most preferably a divalent linking group represented by the general formula (L-3).

In the general formula (1), $R^1$ to $R^{10}$ each may represent a substituent that has a structure other than the general formula (W). Specific examples of the substituent include the specific examples for the substituent R' in the general formulae (L-1), (L-2), (L-10), (L-11), (L-12) and (L-13). Among these, preferred examples of the substituent that has a structure other than the general formula (W) capable of being $R^1$ to $R^{10}$ include a halogen atom, an alkyl group and an aryl group, more preferably a fluorine atom, an alkyl group having from 1 to 3 carbon atoms and a phenyl group, and particularly preferably a fluorine atom and a phenyl group.

In the compound represented by the general formula (1), the number of the substituent represented by $R^1$ to $R^{10}$ except for the substituent represented by the general formula (W) is preferably from 0 to 4, and more preferably from 0 to 2. In the case where the number of substituent represented by the general formula (W) contained in the compound represented by the general formula (1) is 1, the number of the substituent represented by $R^1$ to $R^{10}$ except for the substituent represented by the general formula (W) is preferably 0.

Most of the ordinary compounds having a BBBF-like structure have been compounds containing a chalcogen (e.g., S and Se), but it has been difficult to provide an organic thin film having good film quality and a molecular packing advantageous for carrier transport, from the chalcogen (e.g., S and Se)-containing compound.

Under the circumstances, the invention uses as an organic semiconductor material the compound that has a BBBF skeleton containing oxygen atoms and the substituents having the particular structure, as represented by the general formula (1). It is considered that the organic semiconductor material forms a herringbone structure suitable for carrier transport in the organic thin film facilitating the formation of a two-dimensional overlap of orbitals (the advantage of the herringbone structure for carrier transport is described, for example, in Adv. Mater., vol. 23, pp. 4347-4370 (2011)). Accordingly, it is considered that the compound of the invention achieves good film quality and a high carrier mobility and may be favorably used in an organic thin film transistor.

In the general formula (1) and the general formula (1A) of the invention, at least one of $R^2$, $R^3$, $R^7$ and $R^8$ preferably represents a substituent represented by the general formula (W).

In the case where two or more of $R^2$, $R^3$, $R^7$ and $R^8$ in the general formula (1) and the general formula (1A) each represent a substituent represented by the general formula (W), the substituents represented by the general formula (W) are more preferably substituted at two positions of $R^2$ or $R^3$, and $R^7$ or $R^8$, and particularly preferably substituted at two positions of $R^3$ and $R^8$.

It is considered that the reason why the substitution positions in the general formula (1) are preferably the aforementioned positions is that these positions are advantageous from the standpoint of the HOMO level and the molecular packing in the film. In the case where the substituents are substituted at two positions of $R^3$ and $R^8$, in particular, a high carrier concentration may be obtained.

In the invention, the compound represented by the general formula (1) is preferably a compound represented by one of the following general formulae (2-1), (2-2), (2-3) and (2-4):

General Formula (2-1)

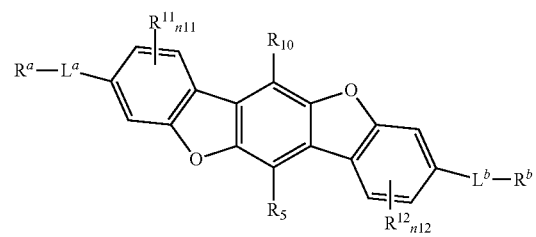

wherein in the general formula (2-1), $L^a$ and $L^b$ each independently represent a divalent linking group represented by one of the following general formulae (L-1) to (L-13) or a divalent linking group containing two or more of divalent linking groups represented by any of the following general formulae (L-1) to (L-13) bonded to each other; $R^a$ and $R^b$ each independently represent a substituted or unsubstituted alkyl group having 2 or more carbon atoms, an oligooxyethylene group having a number of repetition of oxyethylene units of 2 or more, an oligosiloxane group having a number of repetition of siloxane units of 2 or more, or a substituted or unsubstituted trialkylsilyl group, provided that $R^a$ and $R^b$ each are capable of representing a substituted or unsubstituted trialkylsilyl group only in the case where $L^a$ or $L^b$ adjacent to $R^a$ or $R^b$ represents a divalent linking group represented by the following general formula (L-3); $R^{11}$ and $R^{12}$ each independently represent a substituent; and n11 and n12 each independently represent an integer of from 0 to 3, General Formula (2-2)

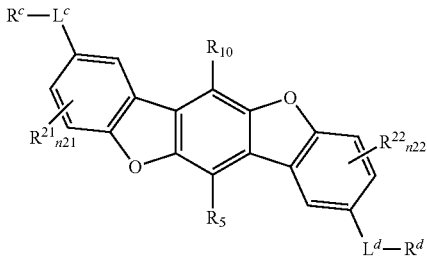

wherein in the general formula (2-2), $L^c$ and $L^d$ each independently represent a divalent linking group represented by one of the following general formulae (L-1) to (L-13) or a divalent linking group containing two or more of divalent linking groups represented by any of the following general formulae (L-1) to (L-13) bonded to each other; $R^c$ and $R^d$ each independently represent a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^c$ and $R^d$ each are capable of representing a substituted or unsubstituted trialkylsilyl group only in the case where $L^c$ or $L^d$ adjacent to $R^c$ or $R^d$ represents a divalent linking group represented by the following general formula (L-3); $R^{21}$ and $R^{22}$ each independently represent a substituent (provided that $R^{21}$ and $R^{22}$ are not a group represented by the general formula (W)); and n21 and n22 each independently represent an integer of from 0 to 3, General Formula (2-3)

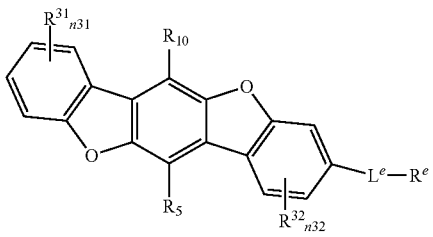

wherein in the general formula (2-3), $L^e$ represents a divalent linking group represented by any of the following general formulae (L-2) to (L-13) or a divalent linking group containing two or more of divalent linking groups represented by any of the following general formulae (L-1) to (L-13) bonded to each other (provided that $L^e$ is not a divalent linking group that contains only two or more of divalent linking groups represented by the general formula (L-1) bonded to each other); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^e$ is capable of representing a substituted or unsubstituted trialkylsilyl group only in the case where $L^e$ adjacent to $R^e$ represents a divalent linking group represented by the following general formula (L-3); $R^{31}$ and $R^{32}$ each independently represent a substituent (provided that $R^{31}$ is not a group represented by the general formula (W)); n31 represents an integer of from 0 to 4; and n32 represents an integer of from 0 to 3, General Formula (2-4)

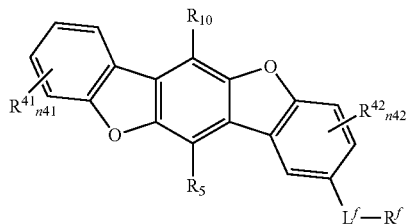

wherein in the general formula (2-4), $L^f$ represents a divalent linking group represented by one of the following general formulae (L-2) to (L-13) or a divalent linking group containing two or more of divalent linking groups represented by any of the following general formulae (L-1) to (L-13) bonded to each other (provided that $L^f$ is not a divalent linking group that contains only two or more of divalent linking groups represented by the general formula (L-1) bonded to each other); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that $R^f$ is capable of representing a substituted or unsubstituted trialkylsilyl group only in the case where $L^f$ adjacent to $R^f$ represents a divalent linking group represented by the following general formula (L-3); $R^{41}$ and $R^{42}$ each independently represent a substituent (provided that $R^{41}$ and $R^{42}$ are not a group represented by the general formula (W)); n41 represents an integer of from 0 to 4; and n42 represents an integer of from 0 to 3:

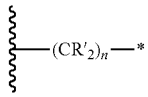
(L-1)

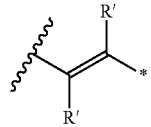
(L-2)

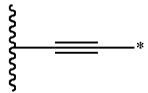
(L-3)

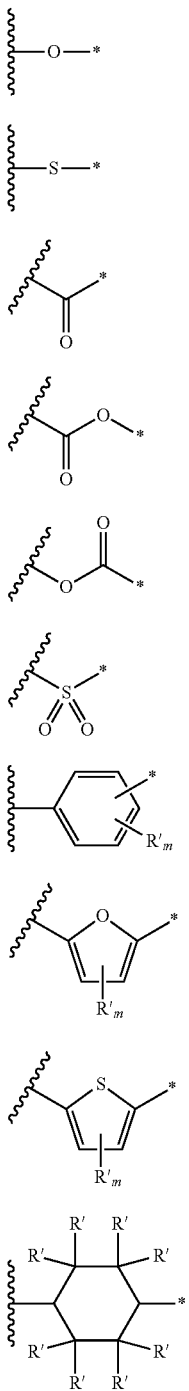

wherein in the general formulae (L-1) to (L-13) in the general formulae (2-1) to (2-4), a position shown by a wave line represents a bonding position to the benzobisbenzofuran skeleton; a position shown by * each independently represent the bonding position to one of $R^a$, $R^b$, $R^c$, $R^d$, $R^e$ and $R^f$ adjacent to the general formulae (L-1) to (L-13); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

In the general formula (2-1) or (2-2), the preferred ranges for $L^a$, $L^b$, $L^c$ and $L^e$ are the same as the preferred range for L in the case where the number of the substituents represented by the general formula (W) contained in the compound represented by the general formula (1) is 2 or more, and in particular, $L^a$, $L^b$, $L^c$ and $L^e$ each preferably independently represent a divalent linking group represented by the general formula (L-1), (L-3), (L-4), (L-5) or (L-13) or a divalent linking group containing two or more of the divalent linking groups bonded to each other.

In the general formula (2-1) or (2-2), the preferred ranges for $R^a$, $R^b$, $R^c$ and $R^d$ are the same as the preferred range for R in the case where the number of the substituents represented by the general formula (W) contained in the compound represented by the general formula (1) is 2 or more.

In the general formula (2-1) or (2-2), the preferred ranges for $R^{11}$, $R^{12}$, $R^{21}$, $R^{22}$, n11, n12, n21 and n22 are the same as the preferred range for $R^1$ to $R^{10}$ in the general formula (1) in the case where the number of the substituents represented by the general formula (W) contained in the compound represented by the general formula (1) is 2 or more.

As shown in the general formulae (2-1) and (2-2), the two -L-R groups represented by the general formula (W) are preferably bonded at symmetric positions with respect to the BBBF skeleton. According to the structure, it is considered that a herringbone structure suitable for carrier transport can be formed in the organic thin film, providing a high carrier mobility.

In the general formula (2-3) or (2-4), the preferred ranges for $L^e$ and $L^f$ are the same as the preferred range for L in the case where the number of the substituent represented by the general formula (W) contained in the compound represented by the general formula (1) is 1, and in particular, $L^e$ and $L^f$ each preferably independently represent a divalent linking group represented by the general formula (L-3), (L-4), (L-5) or (L-13) or a divalent linking group containing two or more of the divalent linking groups bonded to each other.

In the general formula (2-3) or (2-4), the preferred ranges for $R^e$ and $R^f$ are the same as the preferred range for R in the case where the number of the substituent represented by the general formula (W) contained in the compound represented by the general formula (1) is 1.

In the general formula (2-3) or (2-4), the preferred ranges for $R^{31}$, $R^{32}$, $R^{41}$, $R^{42}$, n31, n32, n41 and n42 are the same as the preferred range for $R^1$ to $R^{10}$ in the case where the number of the substituent represented by the general formula (W) contained in the compound represented by the general formula (1) is 1.

In the general formula (2-1), (2-2), (2-3) or (2-4) in the invention, all $R^a$, $R^b$, $R^c$, $R^d$, $R^e$ and $R^f$ each preferably independently represent an alkyl group. When all $R^a$, $R^b$, $R^c$, $R^d$, $R^e$ and $R^f$ each represent an alkyl group, the chemical stability may be enhanced.

The alkyl group used may be any of linear, branched or cyclic, substituted or unsubstituted alkyl groups.

In the general formula (2-1), (2-2), (2-3) or (2-4) in the invention, all $R^a$, $R^b$, $R^c$, $R^d$, $R^e$ and $R^f$ each more preferably independently represent an alkyl group having from 2 to 12 carbon atoms.

It is also preferred that all $R^a$, $R^b$, $R^c$, $R^d$, $R^e$ and $R^f$ each independently represent an alkyl group having from 2 to 7 carbon atoms. When the number of carbon atoms is from 2 to 7, the resulting compound may be enhanced in solubility in a solvent. In the general formula (2-2), in particular, $R^c$ and $R^d$ each preferably independently represent an alkyl group having from 2 to 7 carbon atoms, and thereby the resulting compound may be enhanced in solubility in a solvent. According to the structure, the production efficiency of the organic thin film capable of being applied to an organic thin film transistor may be enhanced, and the production cost may be reduced.

The compound represented by one of the general formulae (2-1), (2-2), (2-3) and (2-4) is preferably a compound represented by one of the following general formulae (2-1'), (2-2'), (2-3') and (2-4'):

General Formula (2-1')

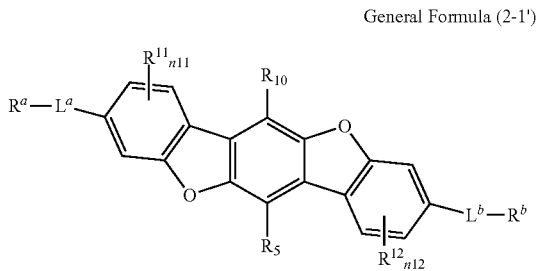

wherein in the general formula (2-1'), $L^a$ and $L^b$ each independently represent a divalent linking group represented by one of the following general formulae (L-1) to (L-13) or a divalent linking group containing two or more of divalent linking groups represented by any of the following general formulae (L-1) to (L-13) bonded to each other; $R^a$ and $R^b$ each independently represent a substituted or unsubstituted alkyl group having from 2 to 12 carbon atoms, an oligooxyethylene group having a number of repetition of oxyethylene units of 2 or more, an oligosiloxane group having a number of repetition of siloxane units of 2 or more, or a substituted or unsubstituted trialkylsilyl group, provided that $R^a$ and $R^b$ each are capable of representing a substituted or unsubstituted trialkylsilyl group only in the case where $L^a$ or $L^b$ adjacent to $R^a$ or $R^b$ represents a divalent linking group represented by the following general formula (L-3); $R^{11}$ and $R^{12}$ each independently represent a substituent; and n11 and n12 each independently represent an integer of from 0 to 3, General Formula (2-2')

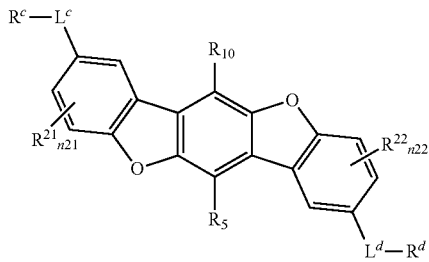

wherein in the general formula (2-2'), $L^c$ and $L^d$ each independently represent a divalent linking group represented by one of the following general formulae (L-1) to (L-13) or a divalent linking group containing two or more of divalent linking groups represented by any of the following general formulae (L-1) to (L-13) bonded to each other; $R^c$ and $R^d$ each independently represent a substituted or unsubstituted alkyl group having from 2 to 7 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^c$ and $R^d$ each are capable of representing a substituted or unsubstituted trialkylsilyl group only in the case where $L^c$ or $L^d$ adjacent to $R^c$ or $R^d$ represents a divalent linking group represented by the following general formula (L-3); $R^{21}$ and $R^{22}$ each independently represent a substituent (provided that $R^{21}$ and $R^{22}$ are not a group represented by the general formula (W)); and n21 and n22 each independently represent an integer of from 0 to 3, General Formula (2-3')

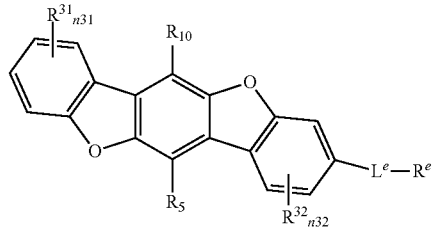

wherein in the general formula (2-3'), $L^e$ represents a divalent linking group represented by one of the following general formulae (L-2) to (L-13) or a divalent linking group containing two or more of divalent linking groups represented by any of the following general formulae (L-1) to (L-13) bonded to each other (provided that $L^e$ is not a divalent linking group that contains only two or more of divalent linking groups represented by the general formula (L-1) bonded to each other); $R^e$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^e$ is capable of representing a substituted or unsubstituted trialkylsilyl group only in the case where $L^e$ adjacent to $R^e$ represents a divalent linking group represented by the following general formula (L-3); $R^{31}$ and $R^{32}$ each independently represent a substituent (provided that $R^{31}$ is not a group represented by the general formula (W)); n31 represents an integer of from 0 to 4; and n32 represents an integer of from 0 to 3, General Formula (2-4')

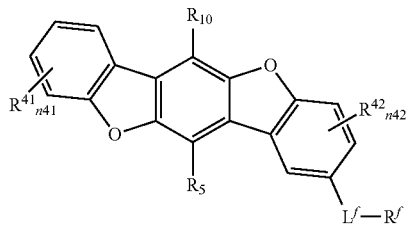

wherein in the general formula (2-4'), $L^f$ represents a divalent linking group represented by one of the following general formulae (L-2) to (L-13) or a divalent linking group containing two or more of divalent linking groups represented by any of the following general formulae (L-1) to (L-13) bonded to each other (provided that $L^f$ is not a divalent linking group that contains only two or more of divalent linking groups represented by the general formula (L-1) bonded to each other); $R^f$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group, provided that $R^f$ is capable of representing a substituted or unsubstituted trialkylsilyl group only in the case where $L^f$ adjacent to $R^f$ represents a divalent linking group represented by the following general formula (L-3); $R^{41}$ and $R^{42}$ each independently represent a substituent (provided that $R^{41}$ and $R^{42}$ are not a group represented by the general formula (W)); n41 represents an integer of from 0 to 4; and n42 represents an integer of from 0 to 3:

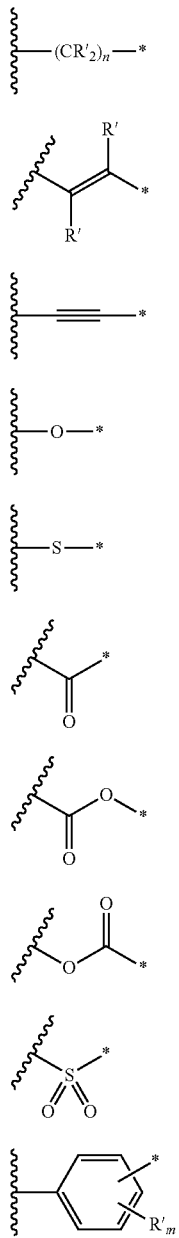

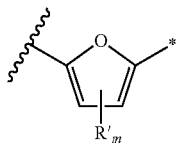

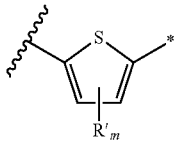

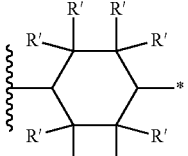

wherein in the general formulae (L-1) to (L-13) in the general formulae (2-1') to (2-4'), a position shown by a wave line represents a bonding position to the benzobisbenzofuran skeleton; a position shown by * each independently represent the bonding position to one of $R^a$, $R^b$, $R^c$, $R^d$, $R^e$ and $R^f$ adjacent to the general formulae (L-1) to (L-13); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

In the general formulae (2-1'), (2-2'), (2-3') and (2-4'), the preferred ranges for the groups are the same as the preferred range for the groups in the general formulae (2-1), (2-2), (2-3) and (2-4).

In the compounds represented by the general formula (1), a compound that has the particular structure is a novel compound. Specifically, in the compounds represented by the general formula (2-1), a compound represented by the general formula (2-1') is a novel compound; in the compounds represented by the general formula (2-2), a compound represented by the general formula (2-2') is a novel compound; in the compounds represented by the general formula (2-3), a compound represented by the general formula (2-3') is a novel compound; and in the compounds represented by the general formula (2-4), a compound represented by the general formula (2-4') is a novel compound.

Specific examples of the compound represented by the general formula (1) are shown below, but the compound represented by the general formula (1) capable of being used in the invention is not construed as being limited to the specific examples.

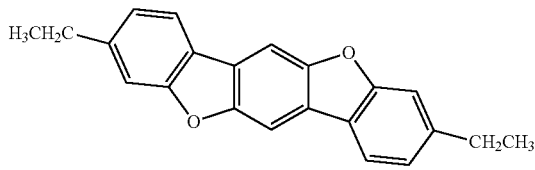

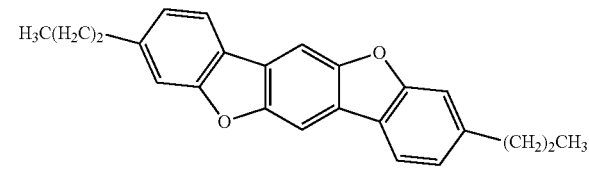

31 32
-continued
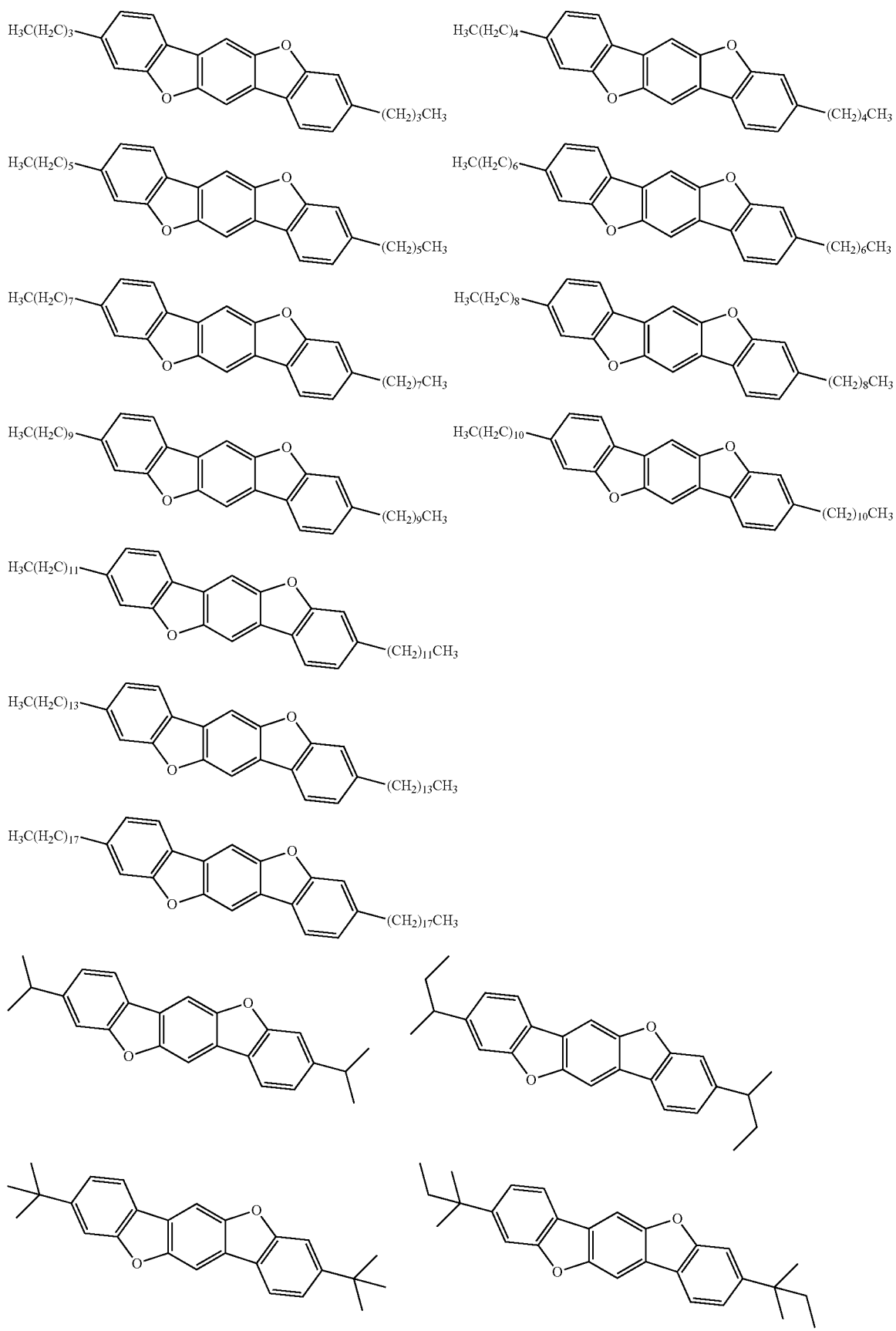

-continued
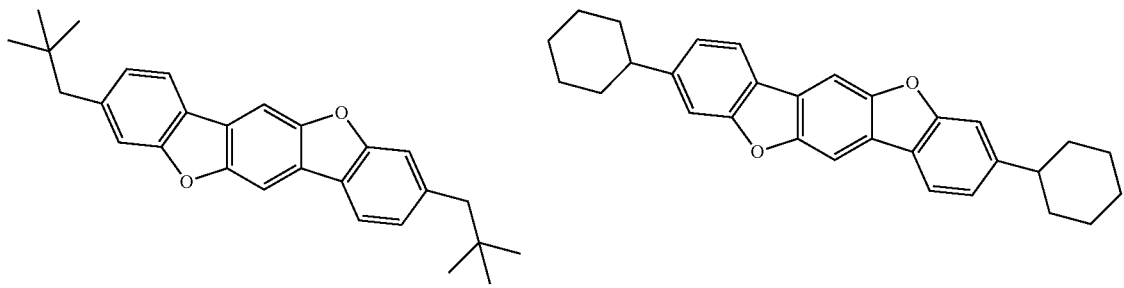
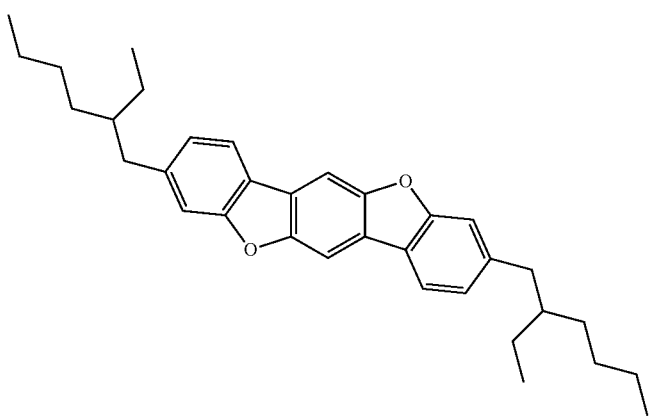
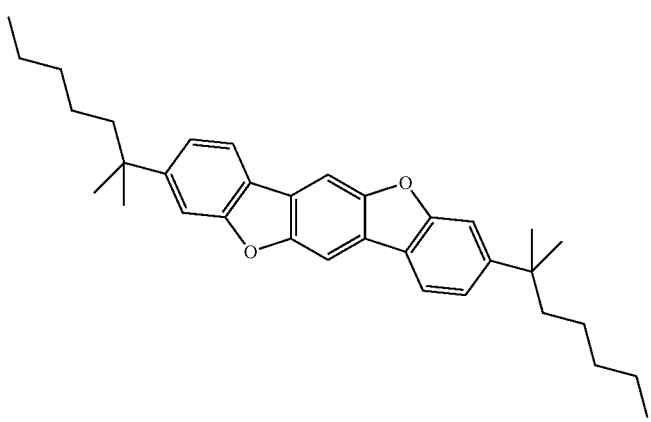
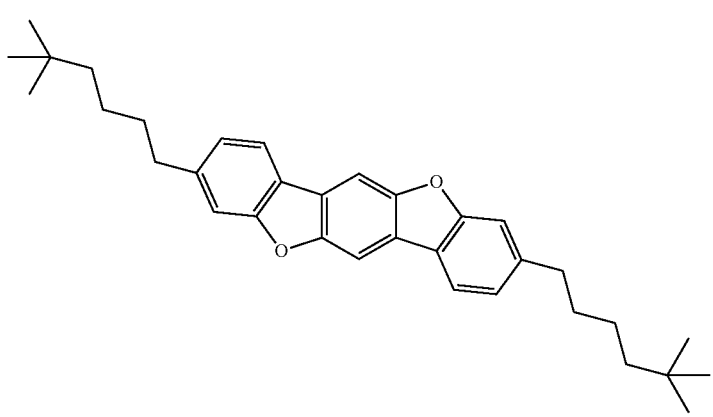

35
-continued
36
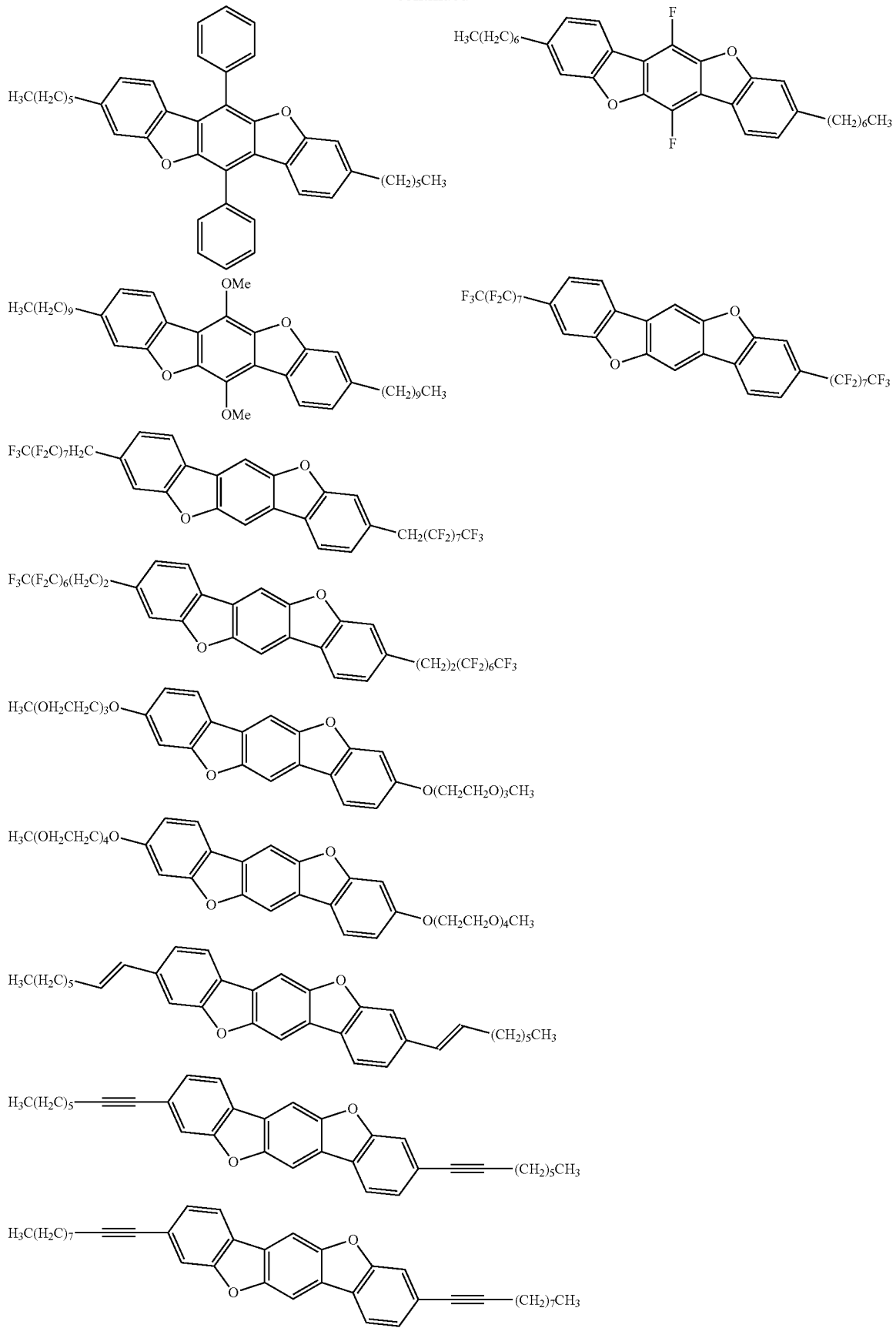

-continued
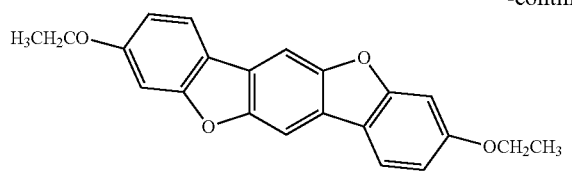
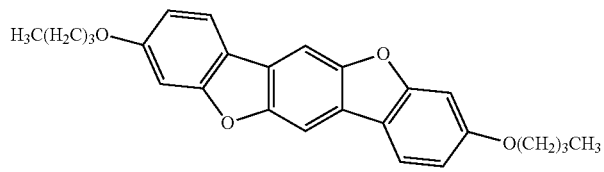
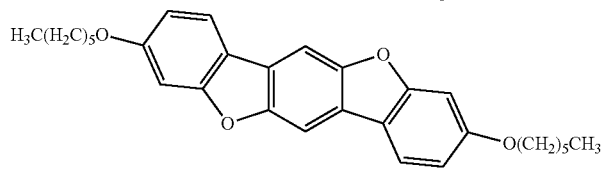
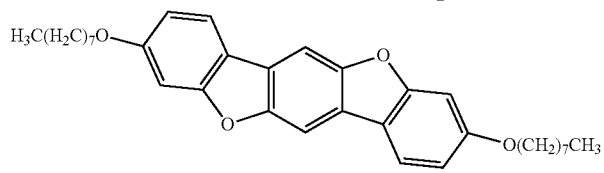
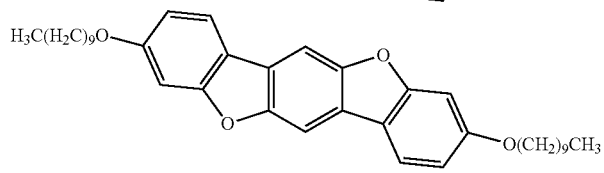
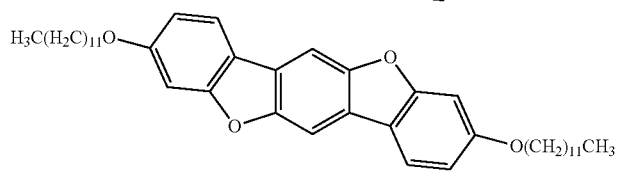
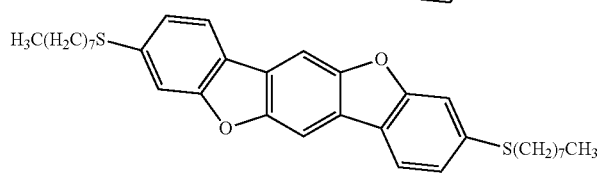
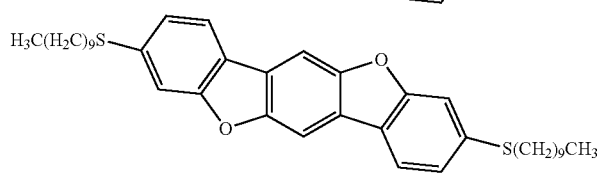
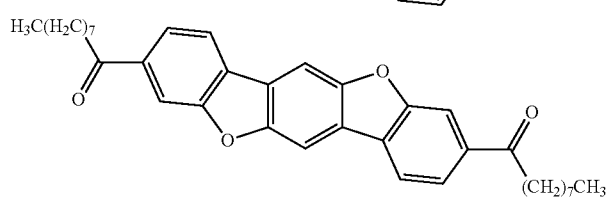
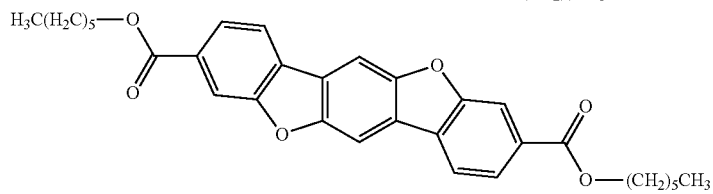

-continued
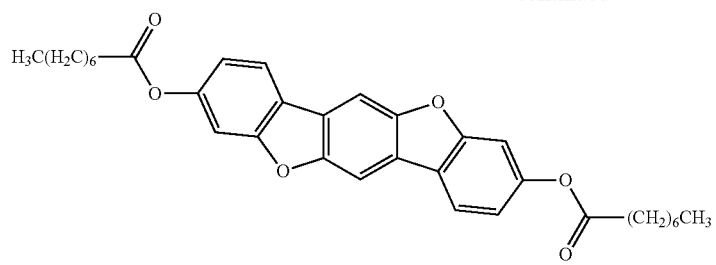
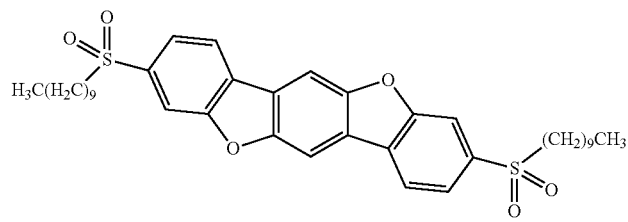
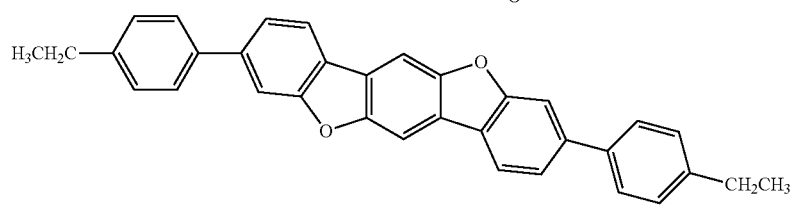
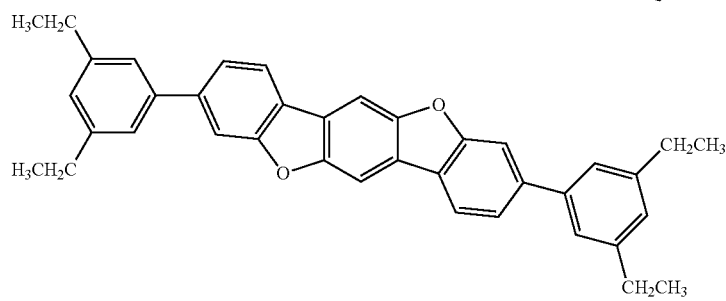
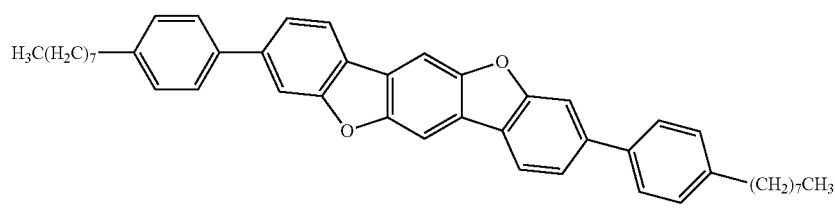
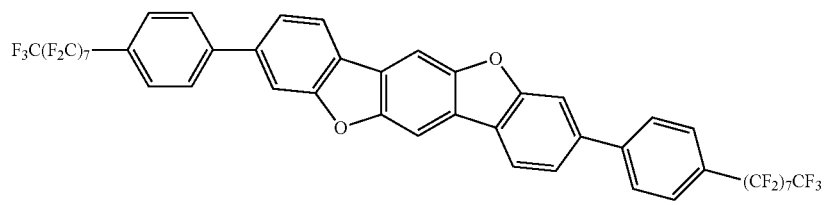
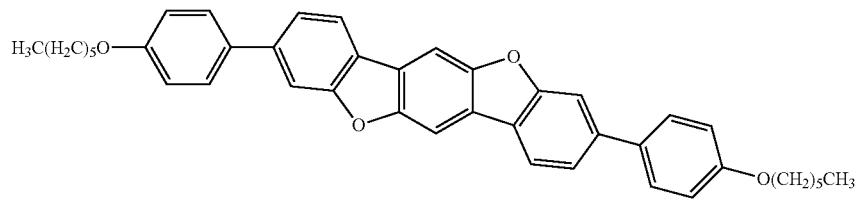

-continued
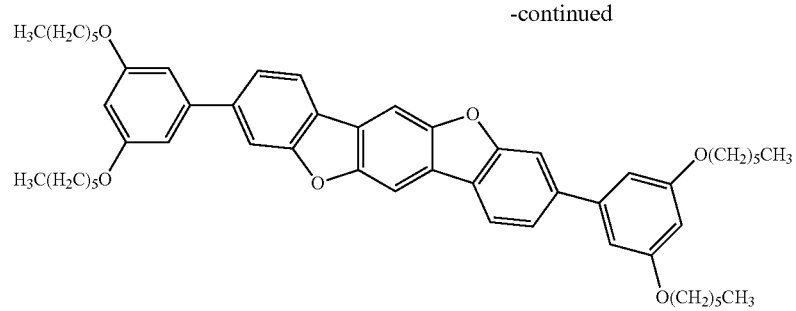
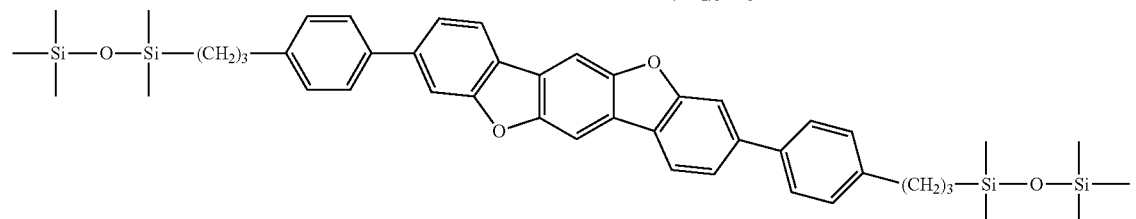
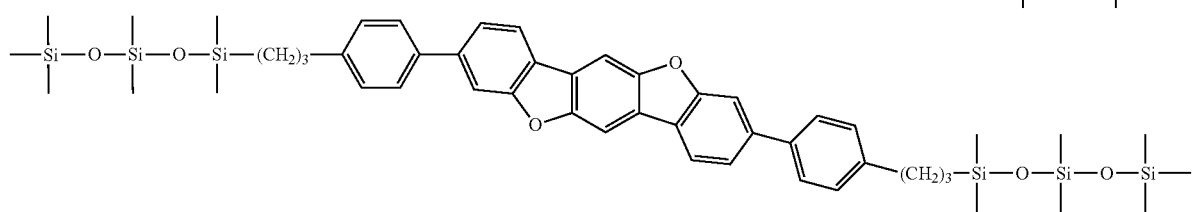
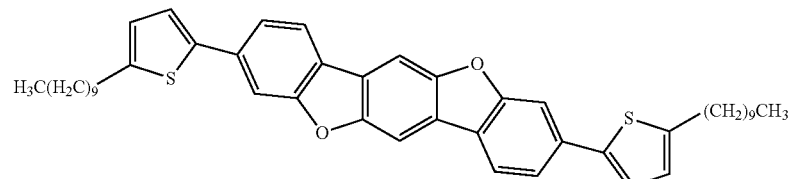
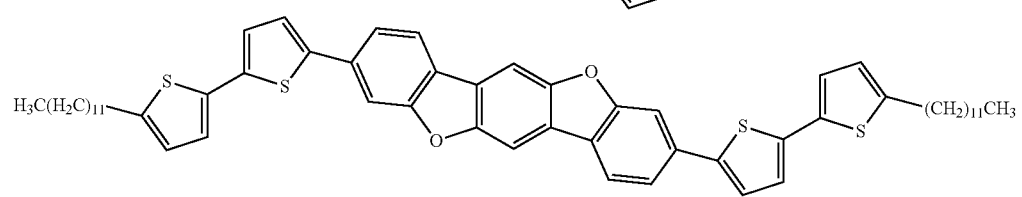
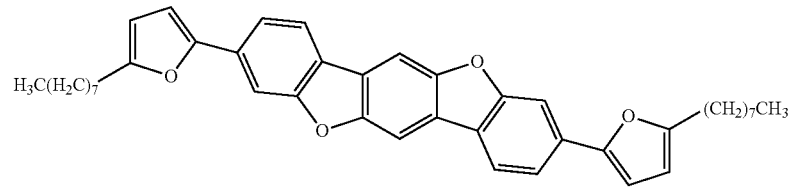
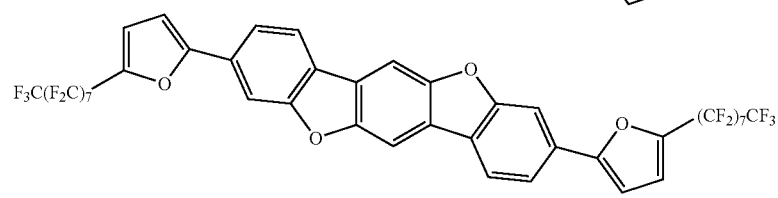
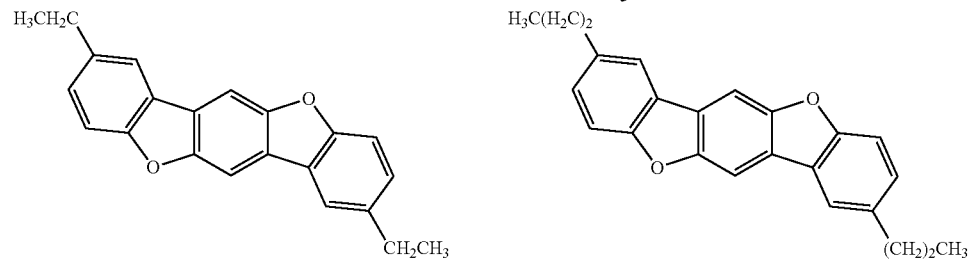

-continued
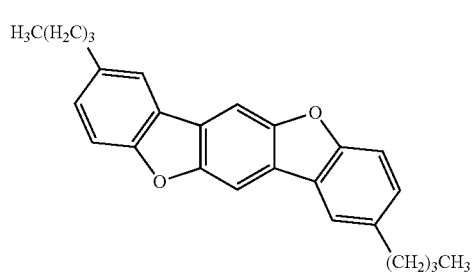
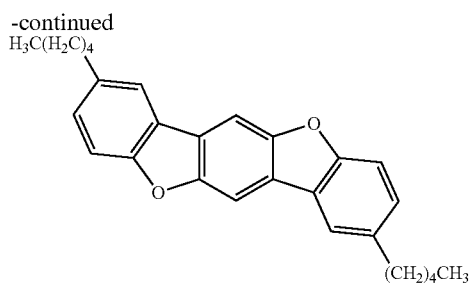
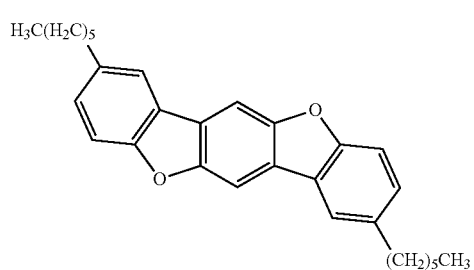
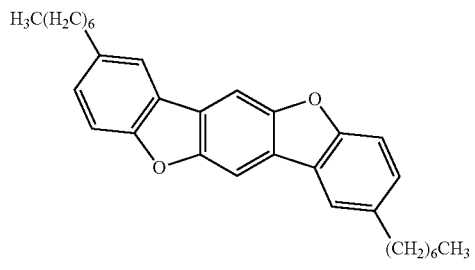
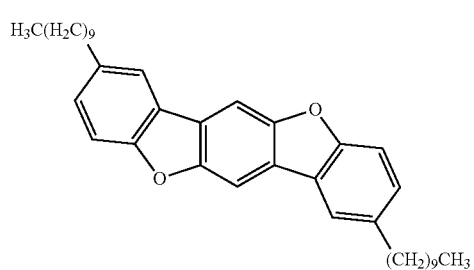
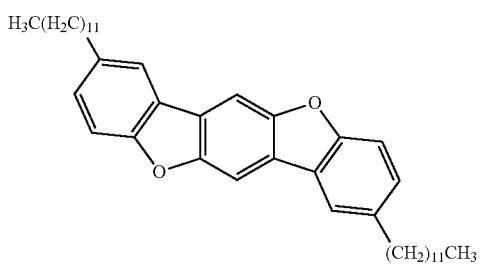
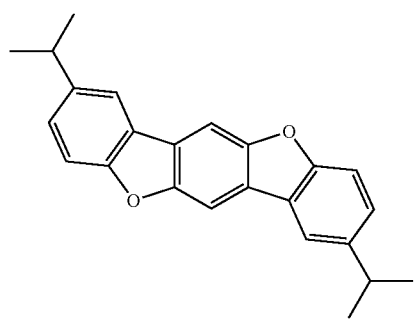
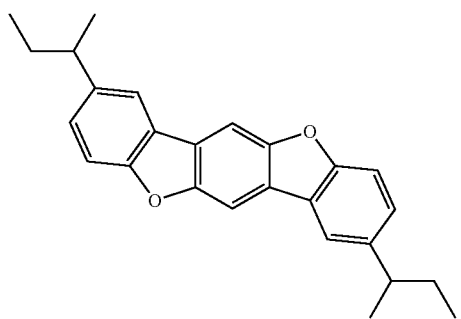
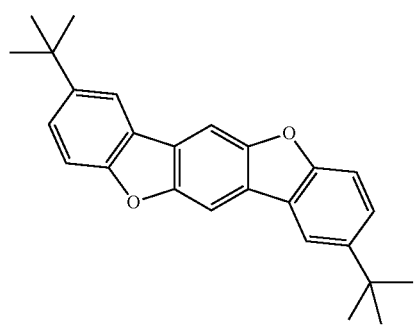
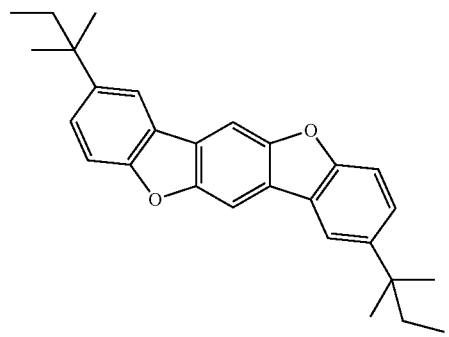

-continued
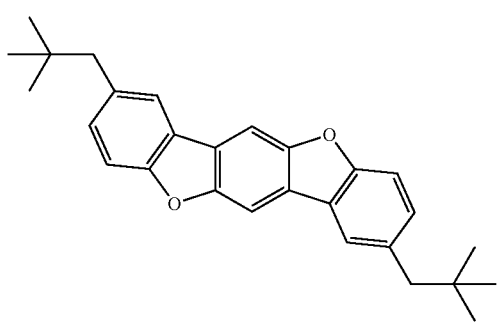
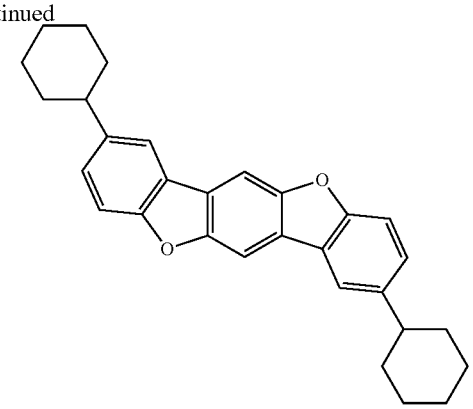
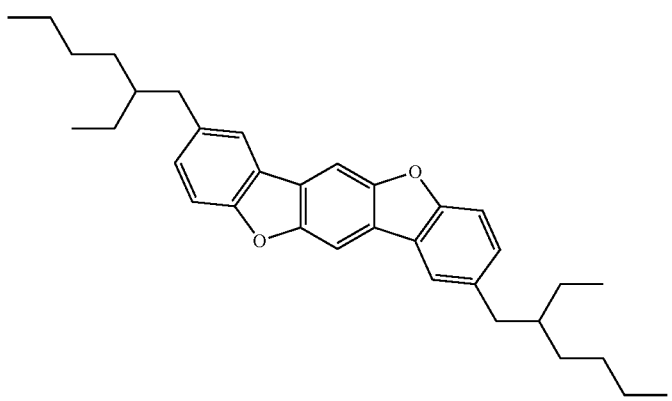
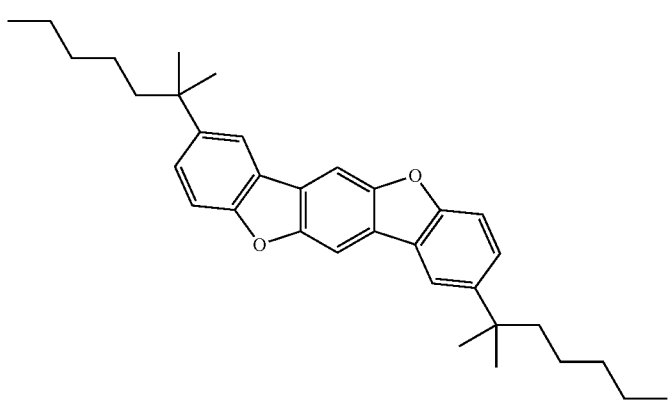
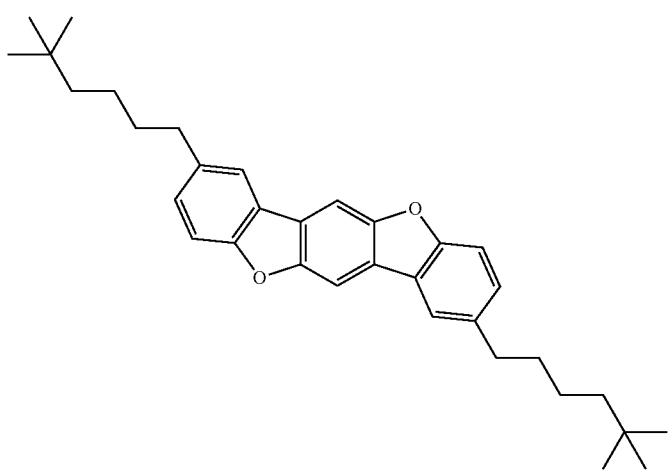

-continued
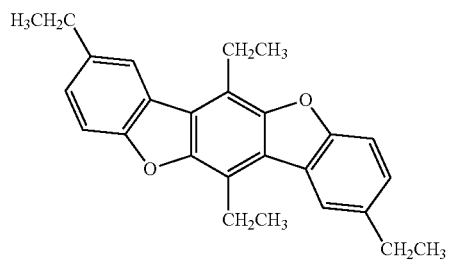
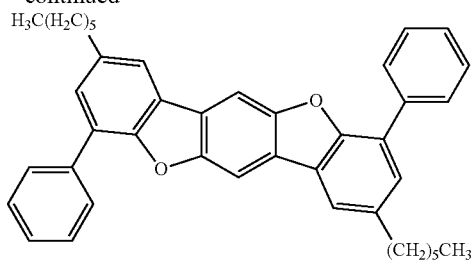
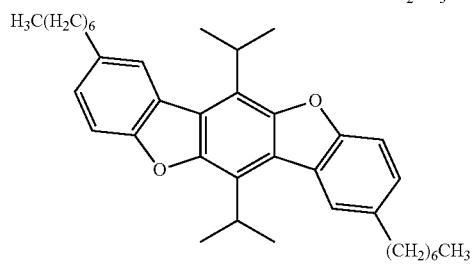
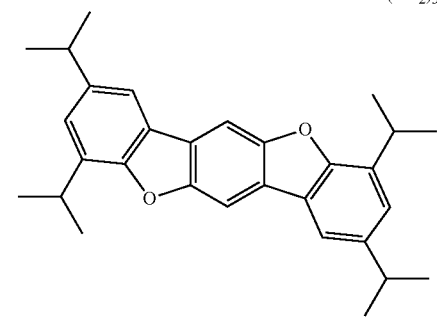
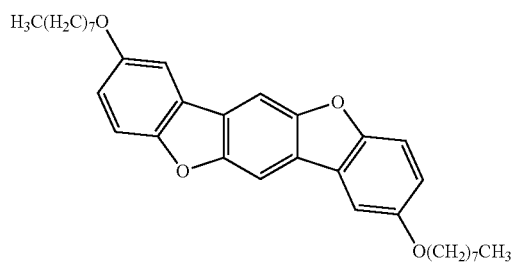
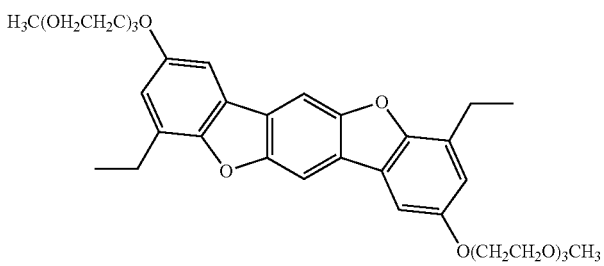
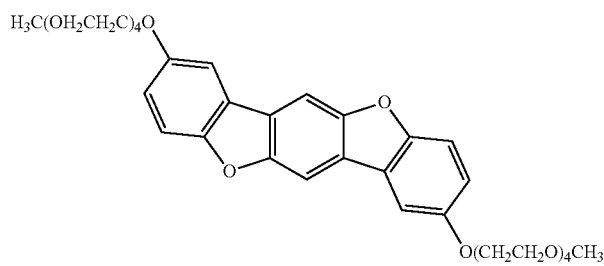
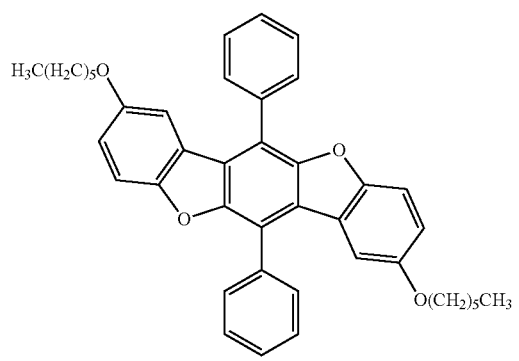
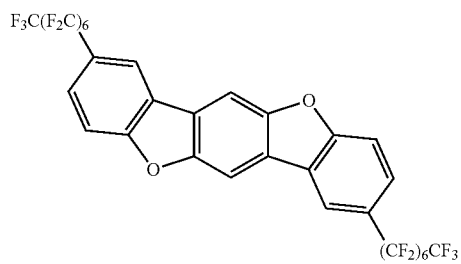
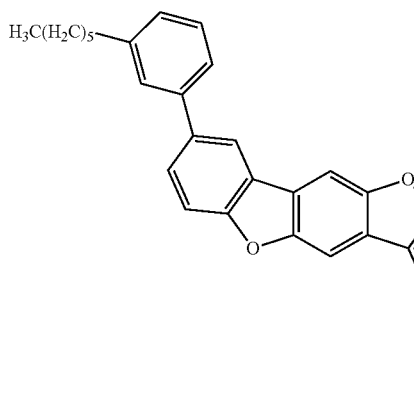

-continued
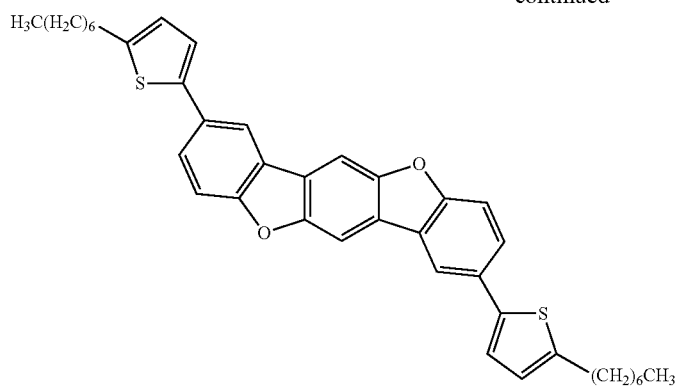
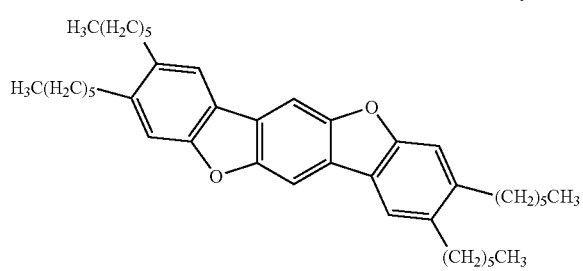
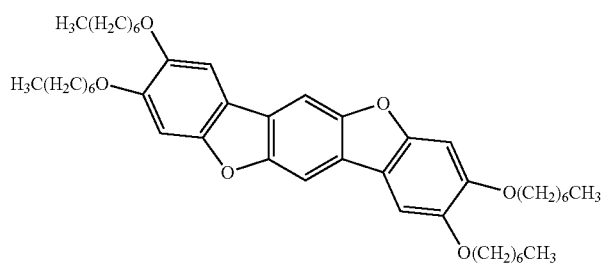
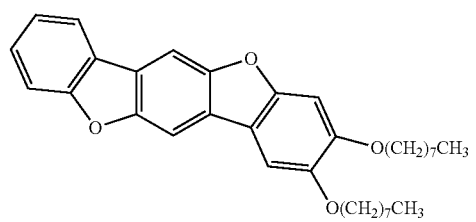
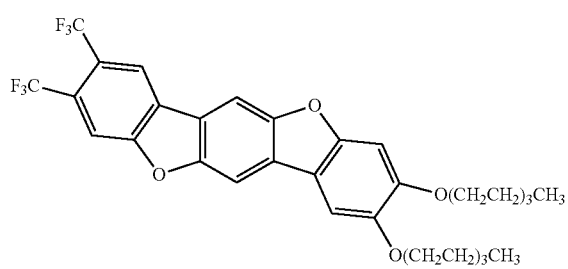
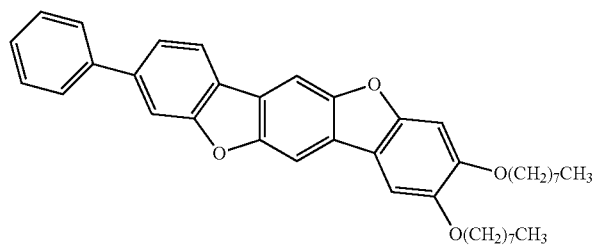
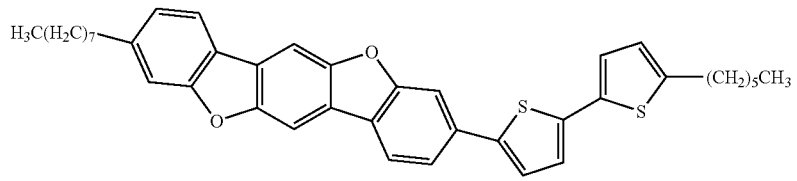

-continued
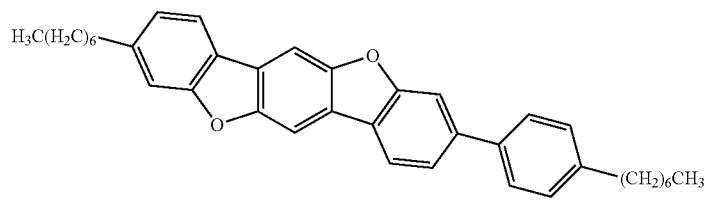
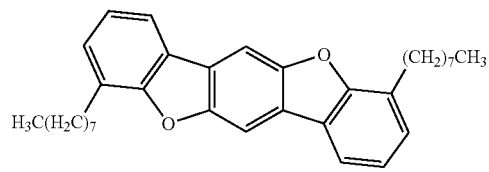
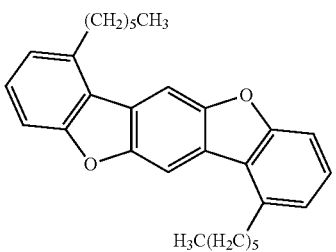
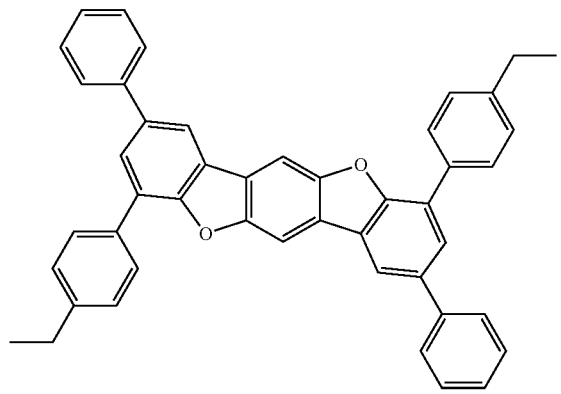
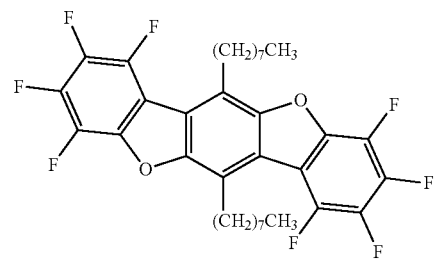
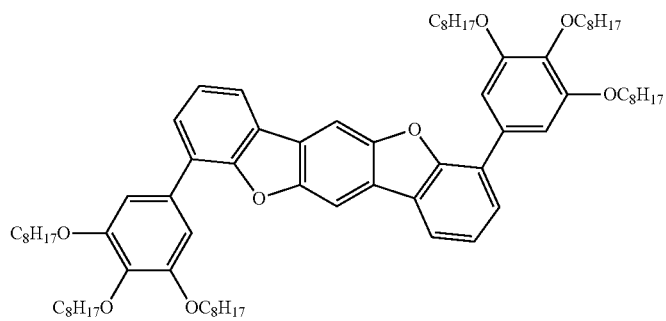
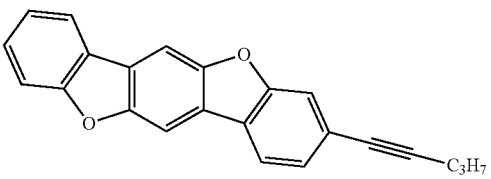
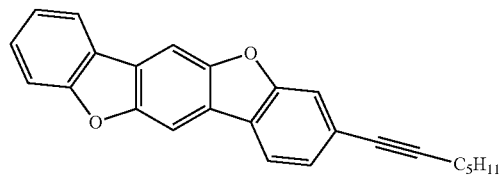
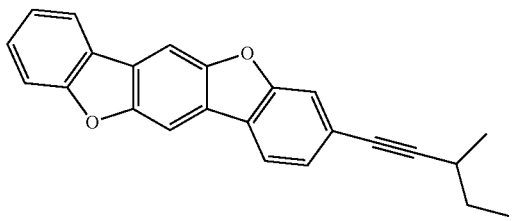
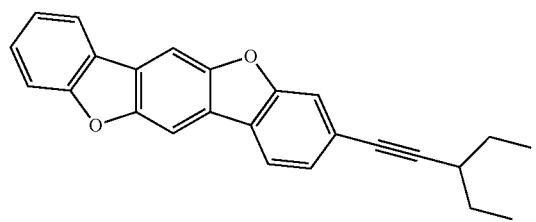
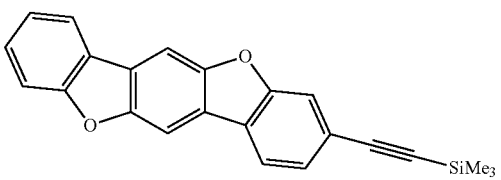

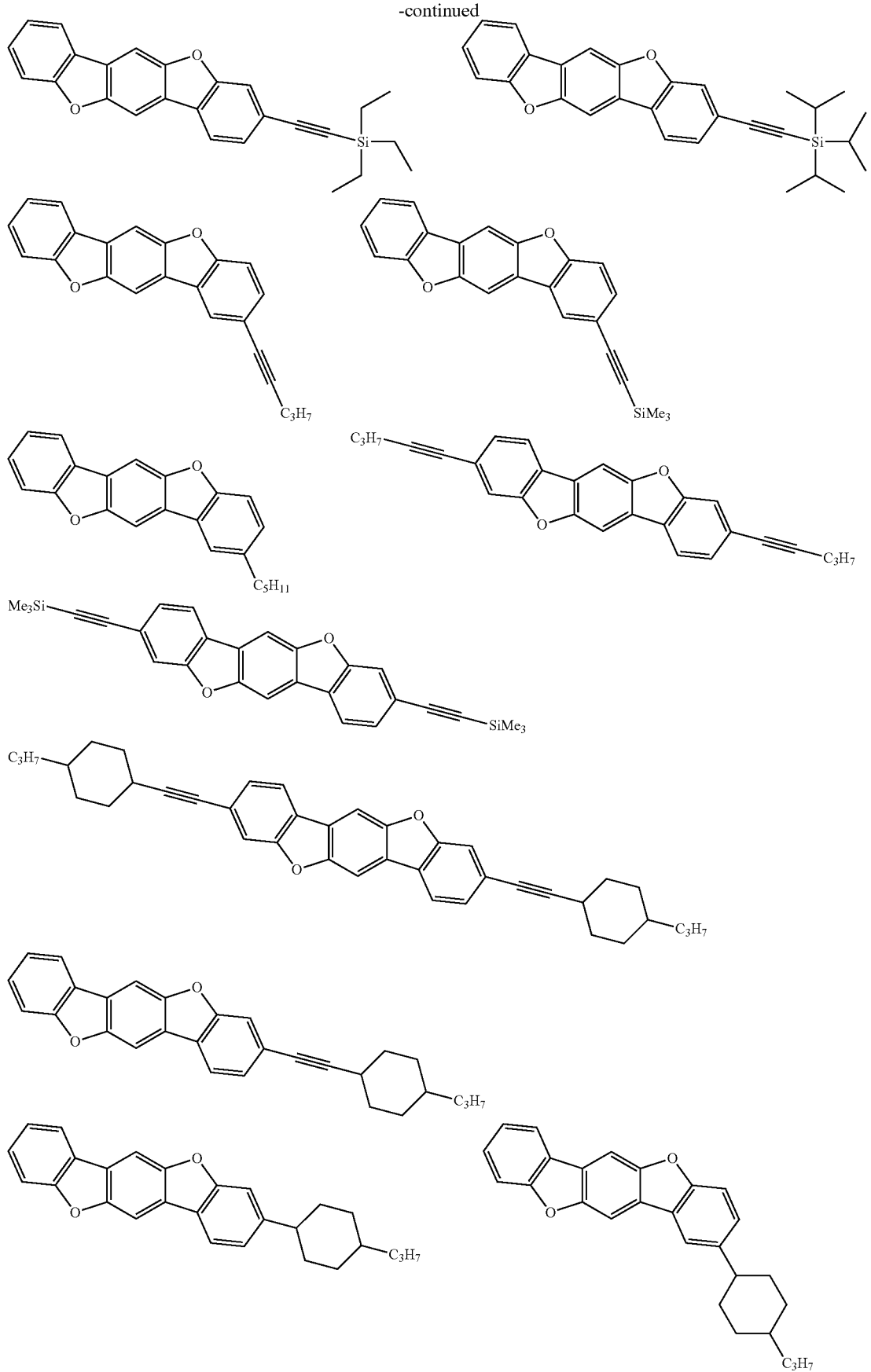

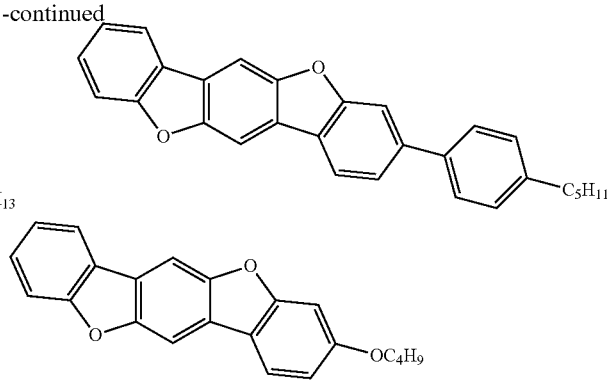
-continued
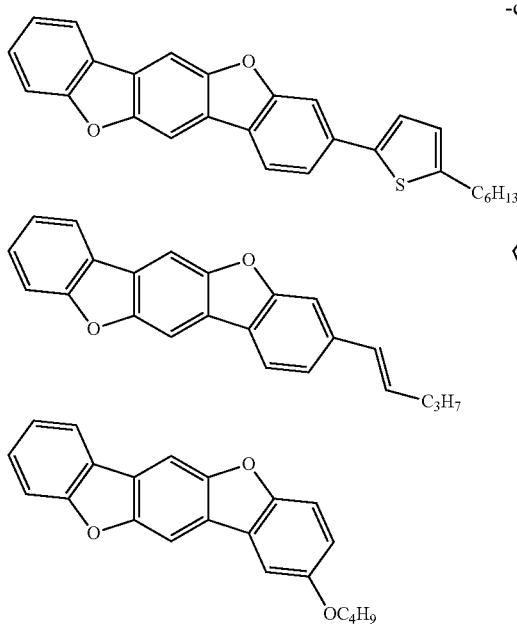

The compound represented by the general formula (1) preferably has a molecular weight of 3,000 or less, more preferably 2,000 or less, further preferably 1,000 or less, and particularly preferably 850 or less. The molecular weight thereof that is the upper limit or less is preferred since the solubility thereof in a solvent may be enhanced.

The molecular weight of the compound is preferably 400 or more, more preferably 450 or more, and further preferably 500 or more, from the standpoint of the stability of the film quality of the thin film.

Synthesis Method

The compound represented by the general formula (1) may be synthesized by combining the known reactions. For example, the compound may be synthesized, for example, by referring to Molecular Electronics and Bioelectronics, The Japan Society of Applied Physics, vol. 22, pp. 9-12 (2011), WO 2009/148016, and the like.

The benzobisbenzofuran ring forming reaction in the invention may be performed in any kind of reaction conditions. The reaction solvent used may be any solvent. An acid or a base is preferably used for accelerating the ring forming reaction, and a base is particularly preferably used therefor. The optimum reaction conditions may vary depending on the structure of the target benzobisbenzofuran derivative and may be determined by referring to the specific reaction conditions shown in the aforementioned literatures.

A synthetic intermediate having various substituents may be synthesized by combining the known reactions. The substituents may be introduced in any of the stages of intermediates. The intermediate after synthesis is preferably purified by column chromatography, recrystallization and the like, and then further purified by sublimation purification. The sublimation purification not only isolates organic impurities but also effectively removes inorganic salts, residual solvents and the like.

Structure of Organic Thin Film Transistor

The organic thin film transistor of the invention contains a semiconductor active layer that contains the compound represented by the general formula (1).

The organic thin film transistor of the invention may further contain additional layers in addition to the semiconductor active layer.

The organic thin film transistor of the invention is preferably used as an organic field effect transistor (FET), and is more preferably used as an insulated gate FET, in which the gate and the channel are insulated from each other.

Preferred embodiments of the structure of the organic thin film transistor of the invention will be described in detail with reference to the drawing, but the invention is not limited to the embodiments.

Laminated Structure

The laminated structure of the organic field effect transistor is not particularly limited, and various known structures may be used therefor.

Examples of the structure of the organic thin film transistor of the invention include a structure that contains a substrate as the lowermost layer having disposed thereon in this order an electrode, an insulator layer, a semiconductor active layer (i.e., an organic semiconductor layer), and two electrodes (i.e., a bottom gate-top contact structure). In this structure, the electrode on the upper surface of the substrate as the lowermost layer is provided on a part of the substrate, and the insulator layer is disposed in such a manner that the insulator layer is in contact with the substrate in the area except for the electrode. The two electrodes provided on the upper surface of the semiconductor active layer are disposed in such a manner that the electrodes are separated from each other.

A structure of a bottom-gate top-contact device is shown in FIG. 1. FIG. 1 is a schematic illustration showing an example of a cross section of the structure of the organic thin film transistor of the invention. In the organic thin film transistor shown in FIG. 1, a substrate 11 is disposed as the lowermost layer, an electrode 12 is disposed on a part of the upper surface of the substrate 11, and an insulator layer 13 is provided in such a manner that the insulator layer 13 covers the electrode 12 and is in contact with the substrate 11 in the area except for the electrode 12. A semiconductor active layer 14 is provided on the upper surface of the insulator layer 13, and two electrodes 15a and 15b separated from each other are disposed on parts of the upper surface of the semiconductor active layer 14.

In the organic thin film transistor shown in FIG. 1, the electrode 12 functions as a gate, and the electrodes 15a and 15b each function as a drain or a source. The organic thin film transistor shown in FIG. 1 is an insulated gate FET, in which the channel, which is an electric current path between the drain and the source, and the gate are insulated from each other.

Examples of the structure of the organic thin film transistor of the invention also include a bottom-gate bottom-contact device.

Figure 2:
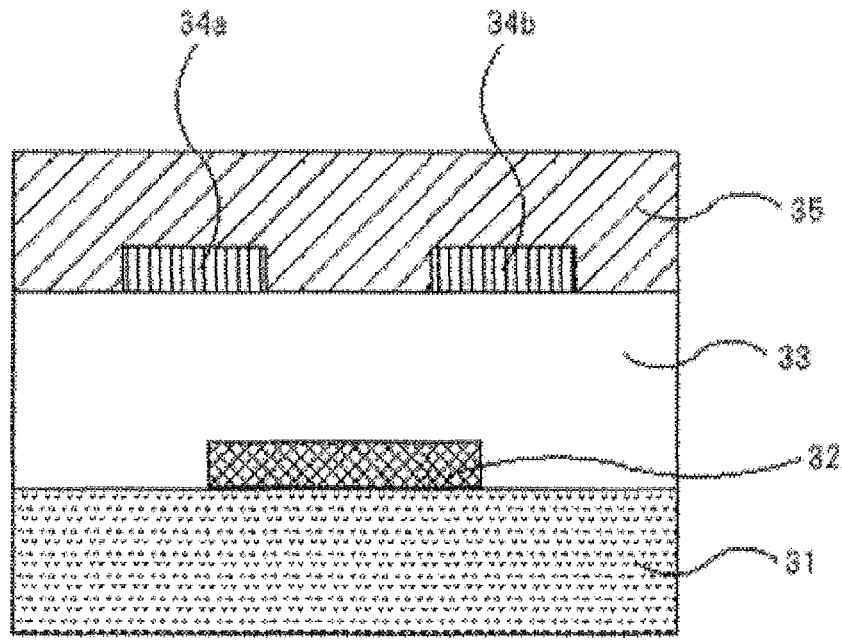
FIG. 2 is a schematic illustration showing a cross section of an organic thin film transistor produced as an FET characteristics measuring substrate in an example of the invention.

A structure of a bottom-gate bottom-contact device is shown in FIG. 2. FIG. 2 is a schematic illustration showing a cross section of a structure of an organic thin film transistor produced as an FET characteristics measuring substrate in an example of the invention. In the organic thin film transistor shown in FIG. 2, a substrate 31 is disposed as the lowermost layer, an electrode 32 is disposed on a part of the upper surface of the substrate 31, and an insulator layer 33 is provided in such a manner that the insulator layer 33 covers the electrode 32 and is in contact with the substrate 31 in the area except for the electrode 32. A semiconductor active layer 35 is provided on the upper surface of the insulator layer 33, and electrodes 34a and 34b are disposed at the lower part of the semiconductor active layer 35.

In the organic thin film transistor shown in FIG. 2, the electrode 32 functions as a gate, and the electrodes 34a and 34b each function as a drain or a source. The organic thin film transistor shown in FIG. 2 is an insulated gate FET, in which the channel, which is an electric current path between the drain and the source, and the gate are insulated from each other.

Examples of the structure of the organic thin film transistor of the invention also preferably include a top-gate top-contact device and a top-gate bottom-contact device, in which an insulator and a gate electrode are disposed in an upper part of a semiconductor active layer.

Thickness

The organic thin film transistor of the invention preferably has a total thickness of the transistor of from 0.1 to 0.5 μm in the case where a further thinner transistor is demanded.

Sealing

The organic thin film transistor device may be entirely sealed with a metallic sealing case, an inorganic material, such as glass and silicon nitride, a high molecular weight material, such as parylene, a low molecular weight material, or the like, for shielding the organic thin film transistor device from the air and water to enhance the storing stability of the organic thin film transistor device.

Preferred embodiments of the layers constituting the organic thin film transistor of the invention will be described below, but the invention is not limited to the embodiments.

Substrate

Material

The organic thin film transistor of the invention preferably contains a substrate.

The material for the substrate is not particularly limited, and known materials may be used. Examples of the material include a polyester film, such as polyethylene naphthalate (PEN) and polyethylene terephthalate (PET), a cycloolefin polymer film, a polycarbonate film, a triacetyl cellulose (TAC) film, a polyimide film, and a film containing the polymer film laminated on an ultrathin glass film, and also include ceramics, silicon, quartz, and glass, and silicon is preferably used.

Electrode

Material

The organic thin film transistor of the invention preferably contains an electrode.

The material constituting the electrode may be any known conductive material without particular limitation, examples of which include a metal, such as Cr, Al, Ta, Mo, Nb, Cu, Ag, Au, Pt, Pd, In, Ni and Nd, an alloy thereof, a carbon material, and a conductive polymer.

Thickness

The thickness of the electrode is not particularly limited and is preferably from 10 to 50 nm.

The gate width (or the channel width) W and the gate length (or the channel length) L are not particularly limited, and the ratio thereof W/L is preferably 10 or more, and more preferably 20 or more.

Insulator Layer

Material

The material constituting the insulator layer is not particularly limited, as far as the material exhibits insulation effect, and examples thereof include silicon dioxide, silicon nitride, a fluorine polymer insulator material, such as PTFE and CYTOP, a polyester insulator material, a polycarbonate insulator material, an acrylic polymer insulator material, an epoxy resin insulator material, a polyimide insulator material, a polyvinyl phenol insulator material and a poly-p-xylene insulator material.

The upper surface of the insulator layer may be surface-treated, and for example, an insulator layer formed of silicon dioxide that is surface-treated by coating hexamethyldisilazane (HMDS) or octadecyltrichlorosilane (OTS) is preferably used.

Thickness

The thickness of the insulator layer is not particularly limited, and in the case where the transistor is demanded to have a small thickness, the thickness of the insulator layer is preferably from 10 to 400 nm, more preferably from 20 to 200 nm, and particularly preferably from 50 to 200 nm.

Semiconductor Active Layer

Material

The organic thin film transistor of the invention has the semiconductor active layer that contains the compound represented by the general formula (1).

The semiconductor active layer may be a layer that is formed of the compound represented by the general formula (1) or may be a layer that contains a polymer binder described later in addition to the compound represented by the general formula (1). The semiconductor active layer may also contain a residual solvent used on forming the layer.

The content of the polymer binder in the semiconductor active layer is not particularly limited, and the polymer binder is preferably used in an amount in a range of from 0 to 95% by mass, more preferably from 10 to 90% by mass, still more preferably from 20 to 80% by mass, and particularly preferably from 30 to 70% by mass.

Thickness

The thickness of the semiconductor active layer is not particularly limited, and in the case where the transistor is demanded to have a small thickness, the thickness of the semiconductor active layer is preferably from 10 to 400 nm, more preferably from 10 to 200 nm, and particularly preferably from 10 to 100 nm.

Organic Semiconductor Material for Non-Light-Emitting Organic Semiconductor Device The invention also relates to an organic semiconductor material for a non-light-emitting organic semiconductor device, containing the compound represented by the general formula (1).

Non-Light-Emitting Organic Semiconductor Device

The non-light-emitting organic semiconductor device referred herein means a device that is not intended to emit light. The non-light-emitting organic semiconductor device is preferably a non-light-emitting organic semiconductor device that uses an electronic element having a layer structure formed of thin films. The non-light-emitting organic semiconductor device encompasses an organic thin film transistor, an organic photoelectric conversion device (such as a solid state image sensing device for an optical sensor, and a solar cell for energy conversion), a gas sensor, an organic rectifying device, an organic inverter, and an information recording device. The organic photoelectric conversion device may be used for both photosensing (e.g., a solid state image sensing device) and energy conversion (e.g., a solar cell). Preferred examples of the non-light-emitting organic semiconductor device include an organic photoelectric conversion device and an organic thin film transistor, and more preferred examples thereof include an organic thin film transistor. Accordingly, the organic semiconductor material for a non-light-emitting organic semiconductor device of the invention is preferably a material for an organic thin film transistor.

Organic Semiconductor Material

The organic semiconductor material referred herein means an organic material that exhibits characteristics of a semiconductor. The organic semiconductor material includes a p-type (hole transporting) organic semiconductor conducting holes as a carrier and an n-type (electron transporting) organic semiconductor conducting electrons as a carrier, as similar to a semiconductor formed of an inorganic material.

The compound represented by the general formula (1) may be used as any of a p-type organic semiconductor material and an n-type organic semiconductor material, and is more preferably used as a p-type organic semiconductor material. The degree of ease of a carrier passing in an organic semiconductor is expressed by a carrier mobility $\mu$. The carrier mobility $\mu$ is preferably larger, and is preferably $1 \times 10^{-3}$ cm$^2$/Vs or more, more preferably $1 \times 10^{-2}$ cm$^2$/Vs or more, particularly preferably $1 \times 10^{-1}$ cm$^2$/Vs or more, and further particularly preferably 1 cm$^2$/Vs or more. The carrier mobility $\mu$ may be obtained from the characteristics of a field effect transistor (FET) device formed with the material or by a time-of-flight (TOF) method.

Organic Semiconductor Thin Film for Non-Light-Emitting Organic Semiconductor Device Material The invention also relates to an organic semiconductor thin film for a non-light-emitting organic semiconductor device, containing the compound represented by the general formula (1).

The organic semiconductor thin film for a non-light-emitting organic semiconductor device of the invention contains the compound represented by the general formula (1), and an embodiment thereof that contains no polymer binder is also preferred.

The organic semiconductor thin film for a non-light-emitting organic semiconductor device of the invention may contain the compound represented by the general formula (1) and a polymer binder.

Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, and copolymers thereof, a photoconductive polymer, such as polyvinylcarbazole and polysilane, and a conductive or semiconductive polymer, such as polythiophene, polypyrrole, polyaniline and poly-p-phenylenevinylene.

The polymer binder may be used solely or as a combination of plural kinds thereof.

The organic semiconductor material and the polymer binder may be mixed uniformly and may be entirely or partially phase-separated, and from the standpoint of the charge mobility, such a structure is most preferred that the organic semiconductor and the binder are phase-separated in the thickness direction in the film since the binder may not inhibit the charge migration of the organic semiconductor.

A polymer binder having a high glass transition temperature is preferred from the standpoint of the mechanical strength of the thin film, and a polymer binder having a structure containing no polar group, a photoconductive polymer and a conductive polymer are preferred from the standpoint of the charge mobility.

The amount of the polymer binder used is not particularly limited, and the polymer binder is preferably used in an amount in a range of from 0 to 95% by mass, more preferably from 10 to 90% by mass still more preferably from 20 to 80% by mass, and particularly preferably from 30 to 70% by mass, in the organic semiconductor thin film for a non-light-emitting organic semiconductor device of the invention.

In the invention, the compound has the aforementioned structure, and thereby an organic thin film having good film quality may be provided. Specifically, the compound obtained in the invention has good crystallinity to provide a sufficient thickness, and thus the resulting organic semiconductor thin film for a non-light-emitting organic semiconductor device of the invention may have good quality.

Film Formation Method

The compound represented by the general formula (1) may be formed into a film on a substrate in any method.

In the formation of the film, the substrate may be heated or cooled, and the film quality and the molecular packing in the film may be controlled by changing the temperature of the substrate. The temperature of the substrate is not particularly limited and is preferably from 0 to 200° C., more preferably from 15 to 100° C., and particularly preferably from 20 to 95° C.

The compound represented by the general formula (1) may be formed into a film on a substrate by any of a vacuum process and a solution process, both of which are preferred.

Specific examples of the vacuum process include a physical vapor phase epitaxial method, such as a vacuum vapor deposition method, a sputtering method, an ion plating method and a molecular beam epitaxial (MBE) method, and a chemical vapor phase deposition (CVD) method, such as a plasma polymerization method, and a vacuum vapor deposition method is particularly preferably used.

The film formation by a solution process herein means that the organic compound is dissolved in a solvent that is capable of dissolving the compound to form a solution, and the film is formed by using the solution. Any ordinary methods may be used, examples of which include a coating method, such as a casting method, a dip coating method, a die coater method, a roll coater method, a bar coater method and a spin coating method, a printing method, such as an ink jet method, a screen printing method, a gravure printing method, a flexography printing method, an offset printing method and a microcontact printing method, and a Langmuir-Blodgett (LB) method, and a casting method, a spin coating method, an ink jet method, a gravure printing method, a flexography printing method, an offset printing method and a microcontact printing method are particularly preferably used.

The organic semiconductor thin film for a non-light-emitting organic semiconductor device of the invention is preferably produced by a solution coating method. In the case where the organic semiconductor thin film for a non-light-emitting organic semiconductor device of the invention contains a polymer binder, the organic semiconductor thin film is preferably formed in such a manner that the materials for forming the layer and the polymer binder are dissolved or dispersed in a suitable solvent to form a coating liquid, which is then coated by a suitable coating method to form the thin film.

A coating liquid for a non-light-emitting organic semiconductor device of the invention capable of being used in the formation of the film by a solution process will be described below.

Coating Liquid for Non-Light-Emitting Organic Semiconductor Device

The invention also relates to a coating liquid for a non-light-emitting organic semiconductor device, containing the compound represented by the general formula (1).

In the case where the thin film is formed on a substrate by a solution process, the materials for forming layer may be dissolved in a suitable organic solvent and/or water to form a coating liquid, which may be then coated by a suitable coating method to form the thin film. Examples of the organic solvent include a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile. The solvent may be used solely or as a combination of plural kinds thereof. Among these, a hydrocarbon solvent, a halogenated hydrocarbon solvent and an ether solvent are preferred, toluene, xylene, mesitylene, tetralin, dichlorobenzene and anisole are more preferred, and toluene, xylene, tetralin and anisole are particularly preferred. The concentration of the compound represented by the general formula (1) in the coating liquid is preferably from 0.1 to 80% by mass, more preferably from 0.1 to 10% by mass, and particularly preferably from 0.5 to 10% by mass, and thereby a film having an arbitrary thickness may be formed.

For forming the film by a solution process, it is necessary to dissolve the materials in the solvent, and it is insufficient that the materials are simply dissolved in the solvent. In general, materials that are formed into a film by a vacuum process may also be dissolved in a solvent to a certain extent. In a solution process, however, after the materials are dissolved in a solvent and then coated, such a process step is necessarily performed that the solvent is evaporated to form a thin film, and a material that is not suitable for a solution process often has high crystallinity and thus is inappropriately crystallized (aggregated) in the process step, so as to fail to provide a favorable thin film. The compound represented by the general formula (1) may be advantageous also in that is unlikely to undergo the crystallization (aggregation).

In one preferred embodiment of the coating liquid for a non-light-emitting organic semiconductor device of the invention, the coating liquid contains the compound represented by the general formula (1) but does not contain a polymer binder.

The coating liquid for a non-light-emitting organic semiconductor device of the invention may contain the compound represented by the general formula (1) and a polymer binder. In this case, the materials for forming layer and the polymer binder are dissolved or dispersed in the aforementioned suitable solvent to form a coating liquid, which is then coated by a suitable coating method to form the thin film. The polymer binder used may be selected from those described above.

EXAMPLES

The features of the invention will be described more specifically with reference to examples and comparative examples below. The materials, the amounts, the ratios, the contents of process, the procedures of process, and the like shown in the examples may be appropriately changed unless the substance of the invention is deviated. Therefore, the scope of the invention is not construed as being limited to the specific examples shown below.

Synthesis Example

The compounds 1 to 27 were synthesized by referring to Molecular Electronics and Bioelectronics, The Japan Society of Applied Physics, vol. 22, pp. 9-12 (2011), WO 2009/148016, and the like.

Production and Evaluation of Device

The materials used for producing a device were purified by sublimation, and it was confirmed that the materials had a purity of 99.5% or more with high performance liquid chromatography (Tosoh TSKgel ODS-100Z) (purity: area ratio of absorption intensity at 254 nm).

Example 1

Formation of Semiconductor Active Layer (Organic Semiconductor Layer) Only with Compound The compound represented by the general formula (1) or a comparative compound (1 mg) and 1,2-dichlorobenzene (1 mL) were mixed and heated to 100° C. The resulting solution was cast on an FET characteristics measuring substrate heated to 100° C. under a nitrogen atmosphere to provide an FET characteristics measuring device. The FET characteristics measuring substrate used was one shown in FIG. 2, which was a silicon substrate having a bottom-gate bottom-contact structure having source and drain electrodes formed of chromium-gold disposed in an interdigitated layout (gate width W=100 mm, gate length L=100 μm) and an insulator film formed of $SiO_2$ (thickness: 200 nm). The FET characteristics were evaluated for the carrier mobility, the change in the mobility after storing under a high temperature and high humidity condition, and the change in the threshold voltage after repeated operation, under a nitrogen atmosphere at an atmospheric pressure by using a semiconductor parameter analyzer (4156C, available from Agilent Technologies, Inc.) having a semiautomatic prober (AX-2000, available from Vector Semiconductor Co., Ltd.). The results obtained are shown in Table 1 below.

(a) Carrier Mobility

While applying a voltage of −100 V between the source electrode and the drain electrode of the FET device, the gate voltage was changed within a range of from 20 to −100 V, and the carrier mobility µ was calculated from the following expression showing the drain current $I_d$.

$$I_d = (w/2L)\mu C_i(V_g - V_{th})^2$$

wherein L represents the gate length, W represents the gate width, $C_i$ represents the capacity of the insulator layer per unit area, $V_g$ represents the gate voltage, and $V_{th}$ represents the threshold voltage. A device that had a carrier mobility of less than $1 \times 10^{-5}$ cm$^2$/Vs was not subjected to the subsequent evaluation for the items (b) and (c) below since the characteristics thereof were too deteriorated.

(b) Change in Mobility after Storing at High Temperature and High Humidity Condition After storing the device at a temperature of 40° C. and a relative humidity of 80% for 24 hours, the device was measured for the carrier mobility in the same manner as in the item (a), and the ratio ($\mu_1/\mu_0$) of the mobility before storing $\mu_0$ and the mobility after storing $\mu_1$ was evaluated by the following three grades. A larger value therefor means higher stability of the device under a high temperature and high humidity condition and thus is preferred. The change in the mobility after storing under a high temperature and high humidity condition is practically demanded to be the grade B or better.

A: $\mu_1/\mu_0 \geq 0.5$
B: $0.1 \leq \mu_1/\mu_0 < 0.5$
C: $\mu_1/\mu_0 < 0.1$ (c) Change in Threshold Voltage after Repeated Operation While applying a voltage of −100 V between the source electrode and the drain electrode and changing the gate voltage repeatedly 100 times within a range of from 20 to −100 V, the same measurement as in the item (a) was performed, and the difference ($|V_1 - V_0|$) between the threshold voltage before repeated operation $V_0$ and the threshold voltage after repeated operation $V_1$ was evaluated by the following three grades. A smaller value therefor means higher stability of the device in repeated operation and thus is preferred. The change in the threshold voltage after repeated operation is practically demanded to be the grade B or better.

A: $|V_1 - V_0| \leq 5$ V
B: $5 \text{ V} \leq |V_1 - V_0| < 10$ V
C: $|V_1 - V_0| > 10$ V The compounds 1 to 27 used as the organic semiconductor material had the following structures.

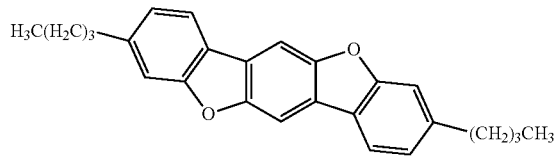

Compound 1

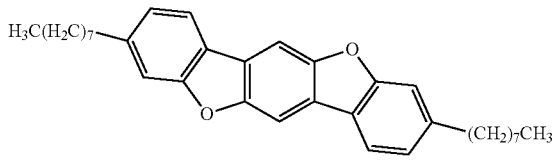

Compound 2

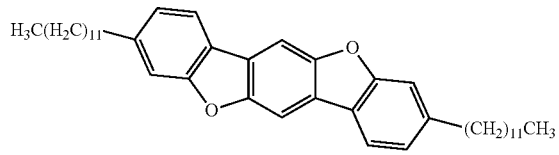

Compound 3

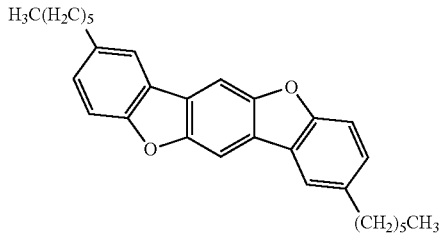

Compound 4

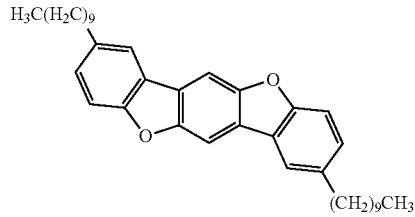

Compound 5

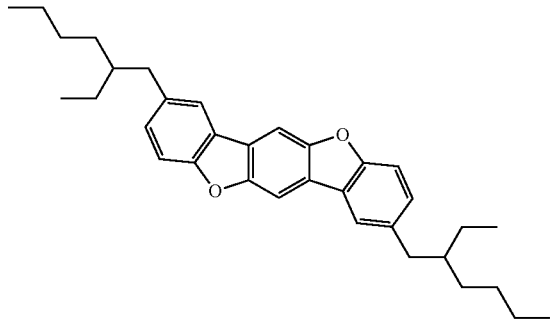

Compound 6

-continued
Compound 7
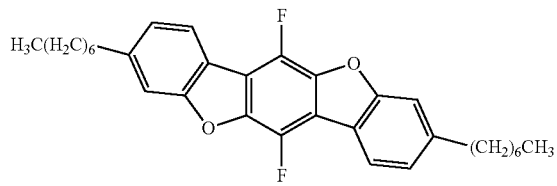
Compound 8
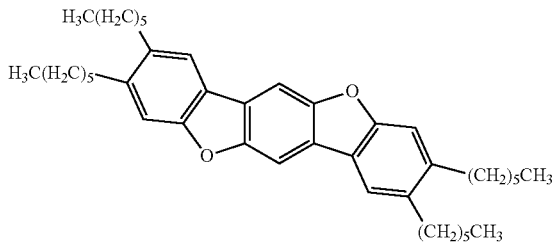
Compound 9
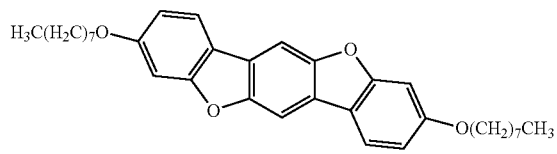
Compound 10
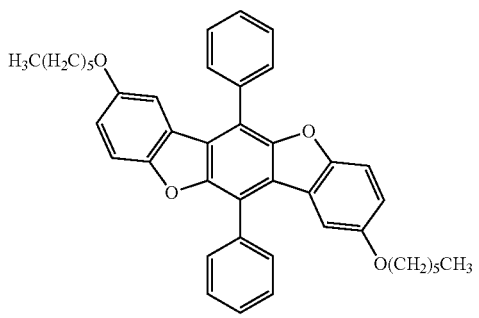
Compound 11
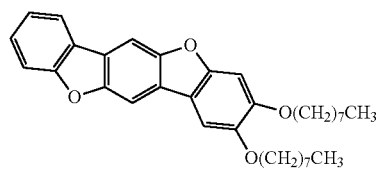
Compound 12
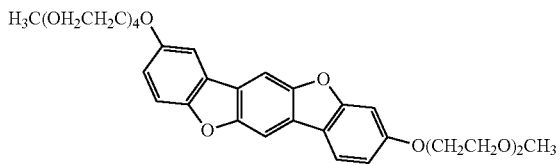
Compound 13
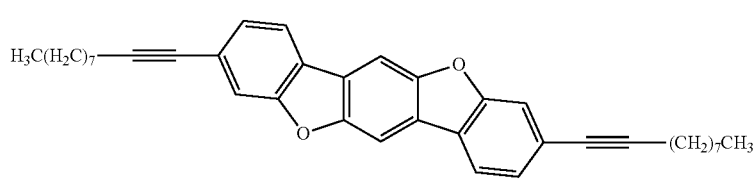
Compound 14
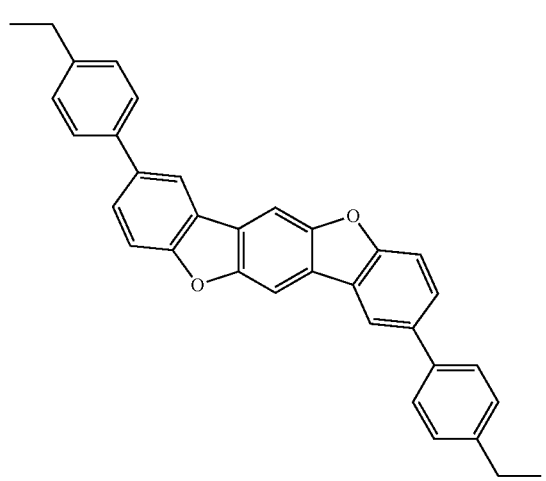

-continued
Compound 15
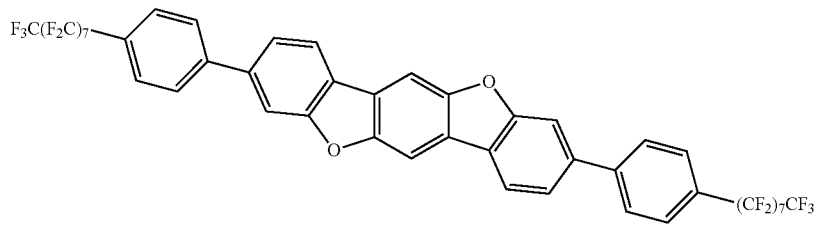
Compound 16
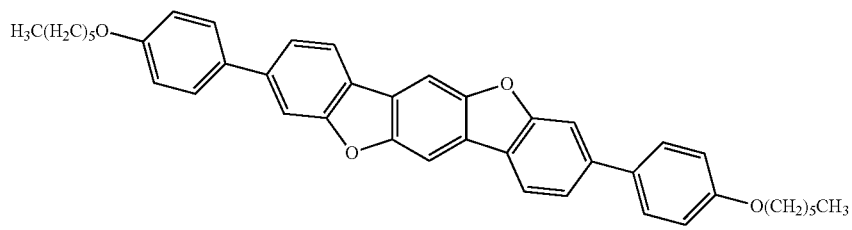
Compound 17
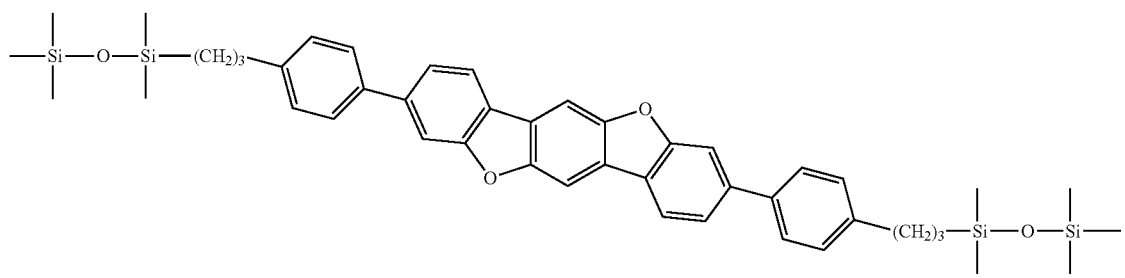
Compound 18
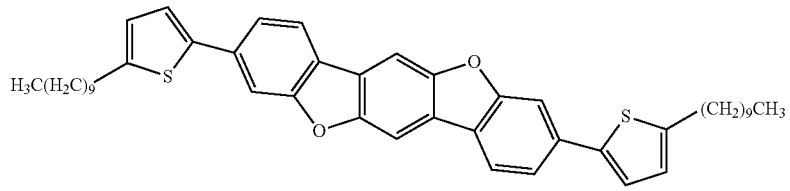
Compound 19
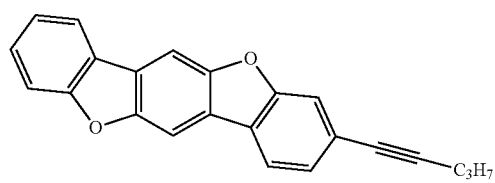
Compound 20
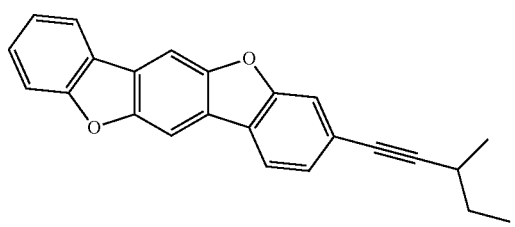
Compound 21
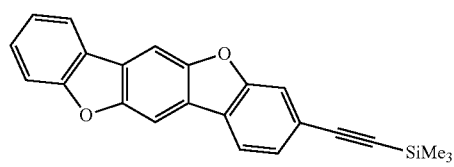
Compound 22
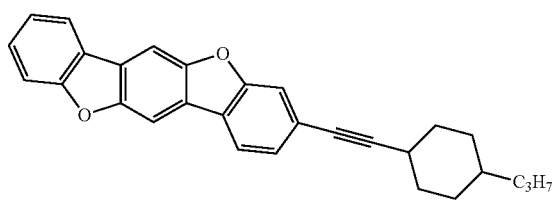
Compound 23
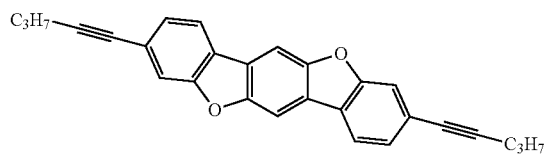
Compound 24
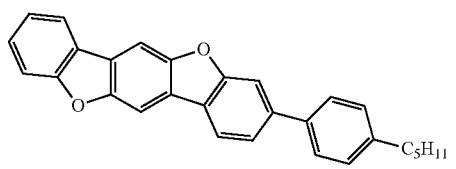

Compound 25
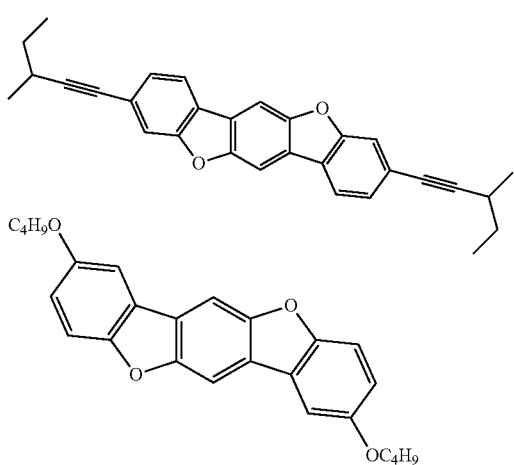
Compound 26
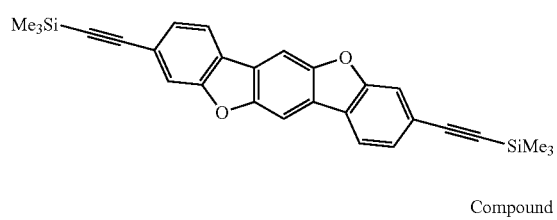
Compound 27
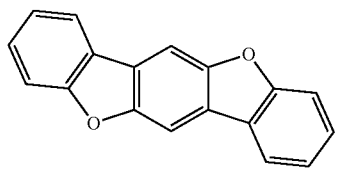
The comparative compounds 1 to 15 used as a comparative organic semiconductor material had the following structures.
Comparative Compound 1
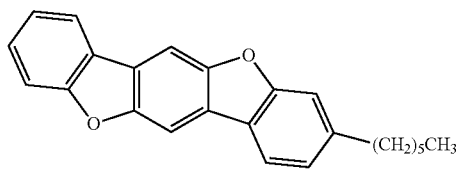
Comparative Compound 2
Comparative Compound 3
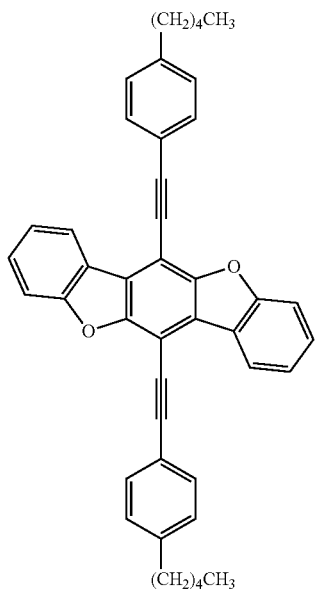
-continued
Comparative Compound 4
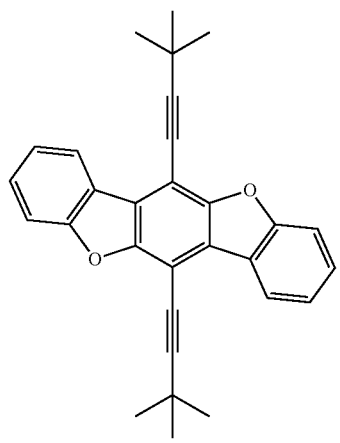
Comparative Compound 5
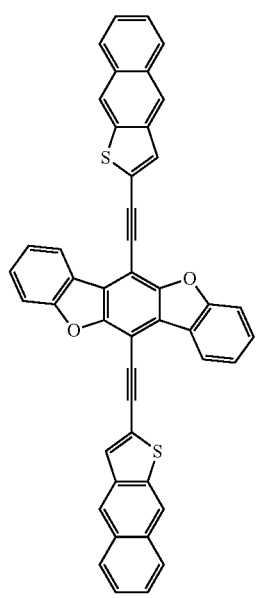

Comparative Compound 6
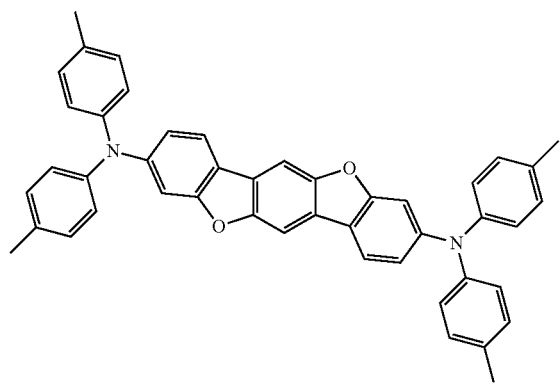
Comparative Compound 7
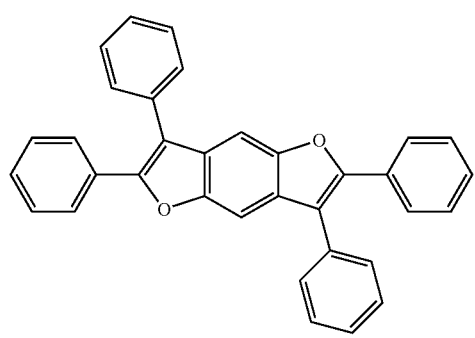
Comparative Compound 8
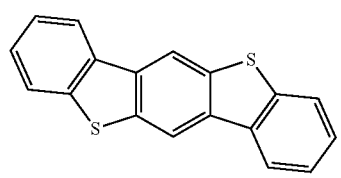
Comparative Compound 9
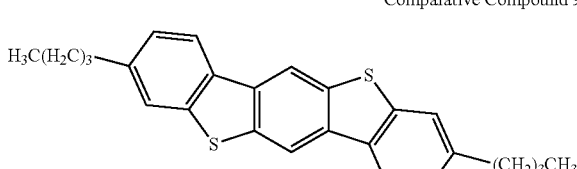
Comparative Compound 10
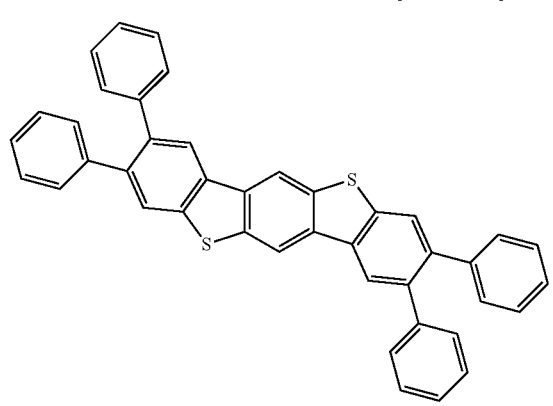
Comparative Compound 11
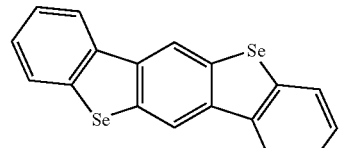
Comparative Compound 12
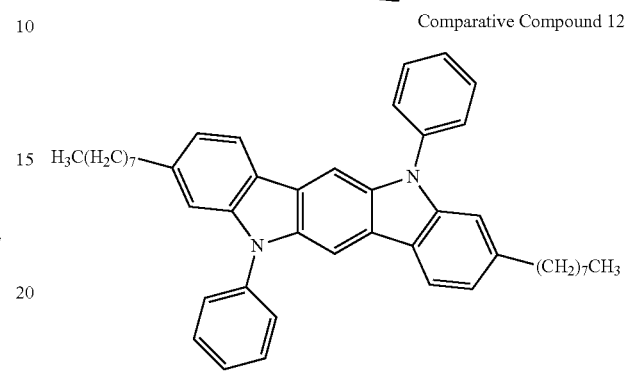
Comparative Compound 13
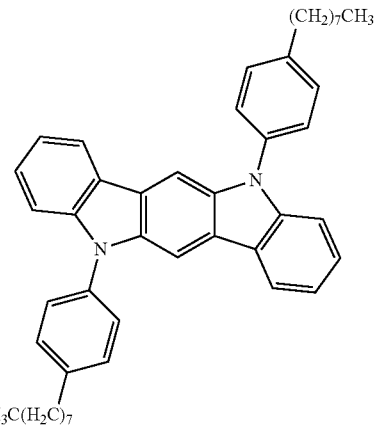
Comparative Compound 14
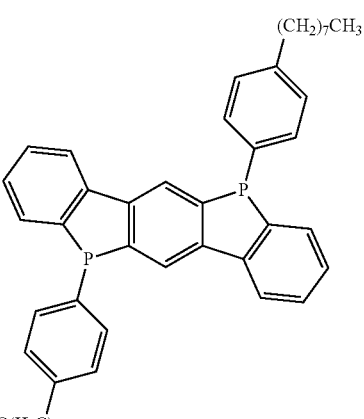
Comparative Compound 15
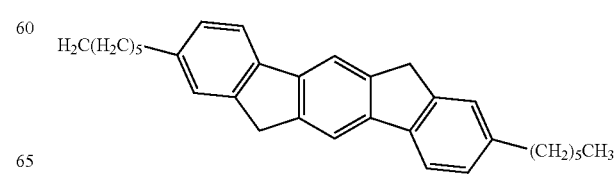

TABLE 1

| Device No. | Organic semiconductor material | Carrier mobility (cm$^2$/Vs) | Change in mobility after storing high temperature and high humidity condition | Change in threshold voltage after repeated operation | Note |
|---|---|---|---|---|---|
| Device 1 | Compound 1 | $1 \times 10^{-2}$ | A | A | invention |
| Device 2 | Compound 2 | $7 \times 10^{-2}$ | A | A | invention |
| Device 3 | Compound 3 | $5 \times 10^{-2}$ | A | A | invention |
| Device 4 | Compound 4 | $2 \times 10^{-2}$ | A | A | invention |
| Device 5 | Compound 5 | $3 \times 10^{-2}$ | A | A | invention |
| Device 6 | Compound 6 | $6 \times 10^{-3}$ | A | B | invention |
| Device 7 | Compound 7 | $9 \times 10^{-3}$ | A | A | invention |
| Device 8 | Compound 9 | $2 \times 10^{-2}$ | B | A | invention |
| Device 9 | Compound 11 | $1 \times 10^{-2}$ | B | B | invention |
| Device 10 | Compound 12 | $5 \times 10^{-3}$ | B | A | invention |
| Device 11 | Compound 13 | $1 \times 10^{-2}$ | B | A | invention |
| Device 12 | Compound 14 | $8 \times 10^{-3}$ | A | A | invention |
| Device 13 | Compound 15 | $2 \times 10^{-2}$ | A | A | invention |
| Device 14 | Compound 17 | $6 \times 10^{-3}$ | B | A | invention |
| Device 15 | Compound 18 | $3 \times 10^{-2}$ | A | A | invention |
| Comparative Device 1 | Comparative Compound 1 | $<1 \times 10^{-5}$ | — | — | comparison |
| Comparative Device 2 | Comparative Compound 2 | $1 \times 10^{-3}$ | C | C | comparison |
| Comparative Device 3 | Comparative Compound 3 | $<1 \times 10^{-5}$ | — | — | comparison |
| Comparative Device 4 | Comparative Compound 4 | $<1 \times 10^{-5}$ | — | — | comparison |
| Comparative Device 5 | Comparative Compound 5 | $<1 \times 10^{-5}$ | — | — | comparison |
| Comparative Device 6 | Comparative Compound 6 | $<1 \times 10^{-5}$ | — | — | comparison |
| Comparative Device 7 | Comparative Compound 7 | $1 \times 10^{-5}$ | — | — | comparison |
| Comparative Device 8 | Comparative Compound 8 | $2 \times 10^{-4}$ | B | C | comparison |
| Comparative Device 9 | Comparative Compound 9 | $5 \times 10^{-5}$ | B | C | comparison |
| Comparative Device 10 | Comparative Compound 10 | $<1 \times 10^{-5}$ | — | — | comparison |
| Comparative Device 11 | Comparative Compound 11 | $3 \times 10^{-4}$ | B | C | comparison |
| Comparative Device 12 | Comparative Compound 12 | $1 \times 10^{-4}$ | C | C | comparison |
| Comparative Device 13 | Comparative Compound 13 | $7 \times 10^{-4}$ | C | C | comparison |
| Comparative Device 14 | Comparative Compound 14 | $<1 \times 10^{-5}$ | — | — | comparison |
| Comparative Device 15 | Comparative Compound 15 | $5 \times 10^{-5}$ | C | C | comparison |

Example 2

Formation of Semiconductor Active Layer (Organic Semiconductor Layer) Only with Compound The compound represented by the general formula (1) or a comparative compound (1 mg) and toluene (1 mL) were mixed and heated to 100° C. The resulting solution was cast on an FET characteristics measuring substrate heated to 90° C. under a nitrogen atmosphere to provide an FET characteristics measuring device. The FET characteristics measuring substrate used was one shown in FIG. 2, which was a silicon substrate having a bottom-gate bottom-contact structure having source and drain electrodes formed of chromium-gold disposed in an interdigitated layout (gate width W=100 nm, gate length L=100 μm) and an insulator film formed of SiO$_2$ (thickness: 200 nm). The FET characteristics were evaluated for the carrier mobility, the change in the mobility after storing under a high temperature and high humidity condition, and the change in the threshold voltage after repeated operation, under a nitrogen atmosphere at an atmospheric pressure by using a semiconductor parameter analyzer (4156C, available from Agilent Technologies, Inc.) having a semiautomatic prober (AX-2000, available from Vector Semiconductor Co., Ltd.). The results obtained are shown in Table 2 below.

TABLE 2

| Device No. | Organic semiconductor material | Carrier mobility (cm$^2$/Vs) | Change in mobility after storing high temperature and high humidity condition | Change in threshold voltage after repeated operation | Note |
|---|---|---|---|---|---|
| Device 21 | Compound 1 | $8 \times 10^{-3}$ | A | A | invention |
| Device 22 | Compound 2 | $2 \times 10^{-1}$ | A | A | invention |

TABLE 2-continued

| Device No. | Organic semiconductor material | Carrier mobility (cm$^2$/Vs) | Change in mobility after storing high temperature and high humidity condition | Change in threshold voltage after repeated operation | Note |
|---|---|---|---|---|---|
| Device 23 | Compound 3 | $3 \times 10^{-2}$ | A | A | invention |
| Device 24 | Compound 4 | $3 \times 10^{-2}$ | A | A | invention |
| Device 25 | Compound 5 | $1 \times 10^{-2}$ | A | A | invention |
| Device 26 | Compound 6 | $4 \times 10^{-3}$ | A | B | invention |
| Device 27 | Compound 7 | $2 \times 10^{-2}$ | A | A | invention |
| Device 28 | Compound 9 | $1 \times 10^{-2}$ | B | A | invention |
| Device 29 | Compound 11 | $2 \times 10^{-2}$ | B | B | invention |
| Device 30 | Compound 12 | $7 \times 10^{-3}$ | B | A | invention |
| Device 31 | Compound 13 | $8 \times 10^{-3}$ | B | A | invention |
| Device 32 | Compound 14 | $9 \times 10^{-3}$ | A | A | invention |
| Device 33 | Compound 15 | $3 \times 10^{-2}$ | A | A | invention |
| Device 34 | Compound 17 | $4 \times 10^{-3}$ | B | A | invention |
| Device 35 | Compound 18 | $2 \times 10^{-2}$ | A | A | invention |
| Device 36 | Compound 19 | $1 \times 10^{-2}$ | B | A | invention |
| Device 37 | Compound 20 | $6 \times 10^{-3}$ | A | A | invention |
| Device 38 | Compound 21 | $8 \times 10^{-2}$ | B | A | invention |
| Device 39 | Compound 22 | $1 \times 10^{-1}$ | A | A | invention |
| Device 40 | Compound 23 | $1 \times 10^{-1}$ | B | A | invention |
| Device 41 | Compound 24 | $6 \times 10^{-2}$ | A | B | invention |
| Device 42 | Compound 25 | $1 \times 10^{-1}$ | A | A | invention |
| Device 43 | Compound 26 | $2 \times 10^{-1}$ | B | A | invention |
| Device 44 | Compound 27 | $2 \times 10^{-2}$ | A | B | invention |
| Comparative Device 21 | Comparative Compound 1 | $<1 \times 10^{-5}$ | — | — | comparison |
| Comparative Device 22 | Comparative Compound 2 | $2 \times 10^{-3}$ | C | C | comparison |
| Comparative Device 23 | Comparative Compound 3 | $<1 \times 10^{-5}$ | — | — | comparison |
| Comparative Device 24 | Comparative Compound 4 | $<1 \times 10^{-5}$ | — | — | comparison |
| Comparative Device 25 | Comparative Compound 5 | $<1 \times 10^{-5}$ | — | — | comparison |
| Comparative Device 26 | Comparative Compound 6 | $<1 \times 10^{-5}$ | — | — | comparison |
| Comparative Device 27 | Comparative Compound 7 | $<1 \times 10^{-5}$ | — | — | comparison |
| Comparative Device 28 | Comparative Compound 8 | $4 \times 10^{-4}$ | B | C | comparison |
| Comparative Device 29 | Comparative Compound 9 | $8 \times 10^{-5}$ | B | C | comparison |
| Comparative Device 30 | Comparative Compound 10 | $<1 \times 10^{-5}$ | — | — | comparison |
| Comparative Device 31 | Comparative Compound 11 | $2 \times 10^{-4}$ | B | C | comparison |
| Comparative Device 32 | Comparative Compound 12 | $3 \times 10^{-4}$ | C | C | comparison |
| Comparative Device 33 | Comparative Compound 13 | $8 \times 10^{-4}$ | C | C | comparison |
| Comparative Device 34 | Comparative Compound 14 | $<1 \times 10^{-5}$ | — | — | comparison |
| Comparative Device 35 | Comparative Compound 15 | $8 \times 10^{-5}$ | C | C | comparison |

Example 3

Formation of Semiconductor Active Layer (Organic Semiconductor Layer) with Compound Represented by General Formula (1) and Binder An FET characteristics measuring substrate was produced in the same manner as in Example 1 except that the coating liquid used was a solution obtained in such a manner that the compound represented by the general formula (1) or a comparative compound (0.5 mg), PaMS (poly(α-methylstyrene), Mw=300,000, produced by Sigma-Aldrich Corporation) and 1,2-dichlorobenzene (1 mL) were mixed and heated to 100° C., and evaluated in the same manner as in Example 1. The results obtained are shown in Table 3 below.

TABLE 3

| Device No. | Organic semiconductor material | Carrier mobility (cm$^2$/Vs) | Change in mobility after storing high temperature and high humidity condition | Change in threshold voltage after repeated operation | Note |
|---|---|---|---|---|---|
| Device 51 | Compound 2 | $5 \times 10^{-2}$ | A | A | invention |
| Device 52 | Compound 4 | $2 \times 10^{-3}$ | A | A | invention |

TABLE 3-continued

| Device No. | Organic semiconductor material | Carrier mobility (cm$^2$/Vs) | Change in mobility after storing high temperature and high humidity condition | Change in threshold voltage after repeated operation | Note |
|---|---|---|---|---|---|
| Device 53 | Compound 8 | $1 \times 10^{-3}$ | A | A | invention |
| Device 54 | Compound 10 | $7 \times 10^{-4}$ | A | A | invention |
| Device 55 | Compound 14 | $4 \times 10^{-3}$ | A | A | invention |
| Device 56 | Compound 16 | $6 \times 10^{-3}$ | A | A | invention |
| Device 57 | Compound 21 | $6 \times 10^{-3}$ | A | A | invention |
| Device 58 | Compound 23 | $4 \times 10^{-2}$ | A | A | invention |
| Device 59 | Compound 25 | $3 \times 10^{-2}$ | A | A | invention |
| Device 60 | Compound 26 | $5 \times 10^{-2}$ | A | A | invention |
| Device 61 | Compound 27 | $8 \times 10^{-3}$ | A | A | invention |
| Comparative Device 16 | Comparative Compound 2 | $7 \times 10^{-5}$ | B | C | comparison |
| Comparative Device 17 | Comparative Compound 8 | $<1 \times 10^{-5}$ | — | — | comparison |
| Comparative Device 18 | Comparative Compound 9 | $<1 \times 10^{-5}$ | — | — | comparison |
| Comparative Device 19 | Comparative Compound 13 | $<1 \times 10^{-5}$ | — | — | comparison |
| Comparative Device 20 | Comparative Compound 15 | $<1 \times 10^{-5}$ | — | — | comparison |

It was found from the results shown in Tables 1 to 3 that the organic thin film transistor using the compound represented by the general formula (1) had a high carrier mobility, a small change in the mobility after storing under a high temperature and high humidity condition, and a small change in the threshold voltage after repeated operation.

On the other hand, it was found that the comparative compounds 1 to 15, which did not satisfy the general formula (1), had a low carrier mobility. It was found that, in particular, the comparative compounds 1, 3 to 7, 10, and 14 had an extremely low carrier mobility. It was also found that the comparative compounds 2, 8, 9, 11 to 13 and 15 exhibited a large change in the mobility after storing under a high temperature and high humidity condition and a large change in the threshold voltage after repeated operation.

The comparative compounds 1 to 3 are the compounds described in Molecular Electronics and Bioelectronics, The Japan Society of Applied Physics, vol. 22, pp. 9-12 (2011), the comparative compound 4 is the compound described in JP-A-2007-88222, the comparative compound 5 is the compound described in JP-A-2009-519595, the comparative compound 6 is the compound described in WO 2006/122630, the comparative compound 7 is the compound described in US 2012/0074396, the comparative compounds 8, 9 and 11 are the compounds described in JP-A-2008-147256, the comparative compounds 10 and 14 are the compounds described in JP-A-2008-81494, the comparative compound 12 is the compound described in US 2006/0128969, the comparative compound 13 is the compound described in US 2006/0125009, and the comparative compound 15 is the compound described in JP-A-2010-229048.

As a result of the observation with an optical microscope and an atomic force microscope (AFM), it was found that the thin films using PaMS as a binder had considerably high smoothness and uniformity of the film. As a result of the comparison between the device 2 and the device 14, the device 14 was higher in smoothness and uniformity of the film. It was understood therefrom that the comparative devices exhibited an extremely low carrier mobility in the composite system with the binder, but the compound represented by the general formula (1) provided such devices that exhibited a good carrier mobility even using with a binder, a small change in the mobility after storing under a high temperature and high humidity condition, a small change in the threshold voltage after repeated operation, and considerably high smoothness and uniformity of the film.

Example 4

Formation of Semiconductor Active Layer (Organic Semiconductor Layer)

A silicon wafer having a gate insulator film formed of SiO$_2$ (thickness: 370 nm) was surface-treated with octyltrichlorosilane.

The compound represented by the general formula (1) or a comparative compound (1 mg) and toluene (1 mL) were mixed and heated to 100° C. to form a coating solution for a non-light-emitting organic semiconductor device. The coating solution was cast on the octylsilane surface-treated silicon wafer heated to 90° C. under a nitrogen atmosphere, thereby forming an organic semiconductor thin film for a non-light-emitting organic semiconductor device.

Gold was vapor-deposited on the surface of the thin film through a mask to form source and drain electrodes, thereby providing an organic thin film transistor device having a bottom-gate top-contact structure having a gate width W of 5 mm and a gate length L of 80 μm. The schematic illustration of the structure is shown in FIG. 1.

The FET characteristics of the organic thin film transistor device of Example 4 were evaluated for the carrier mobility and the change in the threshold voltage after repeated operation, under a nitrogen atmosphere at an atmospheric pressure by using a semiconductor parameter analyzer (4156C, available from Agilent Technologies, Inc.) having a semiautomatic prober (AX-2000, available from Vector Semiconductor Co., Ltd.).

The results obtained are shown in Table 4 below.

TABLE 4

| Device No. | Organic semiconductor material | Carrier mobility (cm$^2$/Vs) | Change in threshold voltage after repeated operation | Note |
| --- | --- | --- | --- | --- |
| Device 71 | Compound 2 | $3 \times 10^{-1}$ | A | invention |
| Device 72 | Compound 3 | $1 \times 10^{-1}$ | A | invention |
| Device 73 | Compound 5 | $4 \times 10^{-2}$ | A | invention |
| Device 74 | Compound 13 | $6 \times 10^{-2}$ | A | invention |
| Device 75 | Compound 18 | $5 \times 10^{-2}$ | A | invention |
| Device 76 | Compound 23 | $2 \times 10^{-1}$ | A | invention |
| Device 77 | Compound 25 | $1 \times 10^{-1}$ | A | invention |
| Device 78 | Compound 27 | $6 \times 10^{-2}$ | A | invention |
| Comparative Device 21 | Comparative Compound 3 | $1 \times 10^{-4}$ | B | comparison |
| Comparative Device 22 | Comparative Compound 4 | $6 \times 10^{-5}$ | B | comparison |
| Comparative Device 23 | Comparative Compound 9 | $8 \times 10^{-3}$ | B | comparison |

It was found from the results shown in Table 4 that the organic thin film transistor devices using the compound represented by the general formula (1) had a high carrier mobility and a small change in the threshold voltage after repeated operation. Accordingly, it was found that the compound represented by the general formula (1) was preferably used as an organic semiconductor material for a non-light-emitting organic semiconductor device.

On the other hand, it was found that the organic thin film transistor devices using the comparative compounds 3, 4 and 9 had a low carrier mobility and a large change in the threshold voltage after repeated operation.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/071322, filed Aug. 7, 2013, and Japanese Patent Application No. 2012-187058 filed on Aug. 27, 2012 and Japanese Patent Application No. 2013-019584 filed on Feb. 4, 2013, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

REFERENCE SIGNS LIST

11: substrate, 12: electrode, 13: insulator layer, 14: organic material layer (semiconductor active layer), 15a, 15b: electrode, 31: substrate, 32: electrode, 33: insulator layer, 34a, 34b: electrode, 35: organic material layer (semiconductor active layer)

What is claimed is:
1. An organic thin film transistor having a semiconductor active layer containing a compound represented by the following general formula (1):

General Formula (1)

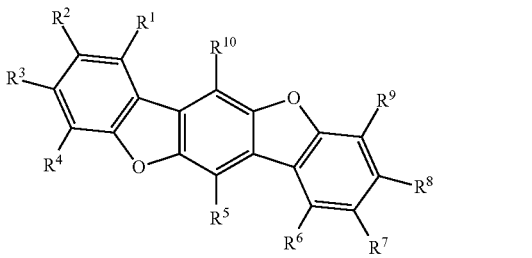

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R                                General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

(L-1)

(L-2)

(L-3)

(L-4)

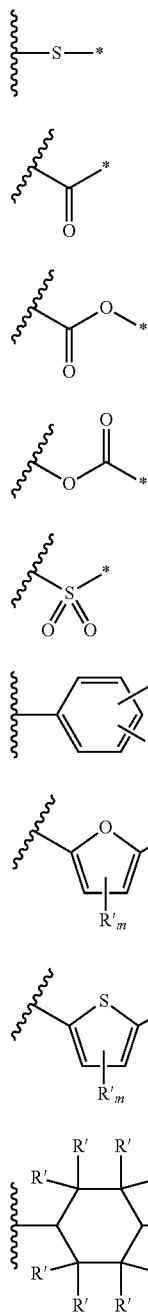

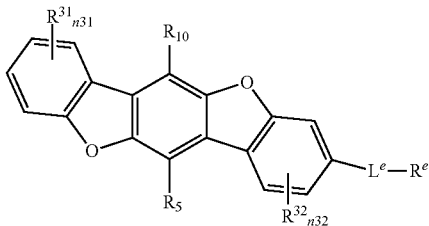

General Formula (2-3)

wherein in the general formula (2-3), $L^e$ represents a divalent linking group represented by the following general formula (L-3'); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the general formula (W)); $R_5$ and $R_{10}$ each independently represent a hydrogen atom or a substituent; n31 represents an integer of from 0 to 4; and n32 represents an integer of from 0 to 3,

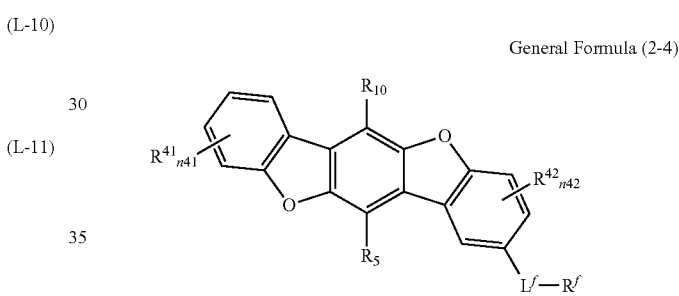

General Formula (2-4)

wherein in the general formula (2-4), $L^f$ represents a divalent linking group represented by the following general formula (L-3'); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the general formula (W)); $R_5$ and $R_{10}$ each independently represent a hydrogen atom or a substituent; n41 represents an integer of from 0 to 4; and n42 represents an integer of from 0 to 3:

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent, wherein the compound represented by the general formula (1) is a compound represented by one of the following general formulae (2-3) and (2-4):

(L-3')

wherein in the general formula (L-3') in the general formulae (2-3) and (2-4), a position shown by a wave line represents a bonding position to the benzobisbenzofuran skeleton; a position shown by * represents the bonding position to one of $R^e$ and $R^f$ adjacent to the general formula (L-3').

2. The organic thin film transistor according to claim 1, wherein in the general formula (2-3) or (2-4), $R^e$ and $R^f$ each independently represent an alkyl group.

3. The organic thin film transistor according to claim 1, wherein in the general formula (2-3) or (2-4), $R^e$ represents an alkyl group having from 2 to 12 carbon atoms; and $R^f$ represents an alkyl group having from 2 to 12 carbon atoms.

4. A compound represented by one of the following general formulae (2-3') or (2-4'):

General Formula (2-3')

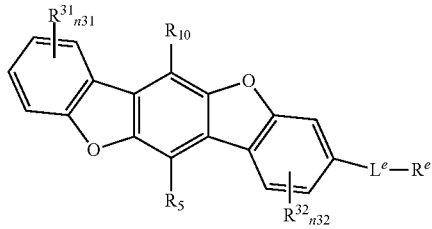

wherein in the general formula (2-3'), $L^e$ represents a divalent linking group represented by the following general formula (L-3'); $R^e$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the following general formula (W)); $R_5$ and $R_{10}$ each independently represent a hydrogen atom or a substituent; n31 represents an integer of from 0 to 4; and n32 represents an integer of from 0 to 3, General Formula (2-4')

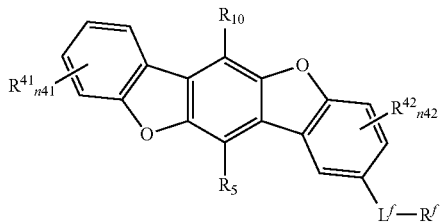

wherein in the general formula (2-4'), $L^f$ represents a divalent linking group represented by the following general formula (L-3'); $R^f$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the following general formula (W)); $R_5$ and $R_{10}$ each independently represent a hydrogen atom or a substituent; n41 represents an integer of from 0 to 4; and n42 represents an integer of from 0 to 3:

(L-3')

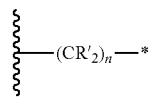

wherein in the general formula (L-3') a position shown by a wave line represents a bonding position to the benzobisbenzofuran skeleton; a position shown by * represents the bonding position to one of $R^e$ and $R^f$ adjacent to the general formula (L-3');

-L-R      General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

(L-1)
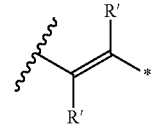

(L-2)
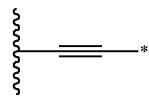

(L-3)
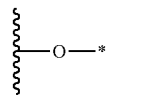

(L-4)
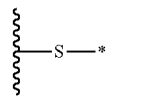

(L-5)
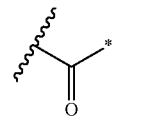

(L-6)
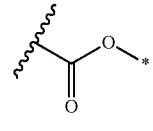

(L-7)
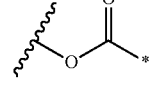

(L-8)
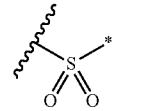

(L-9)

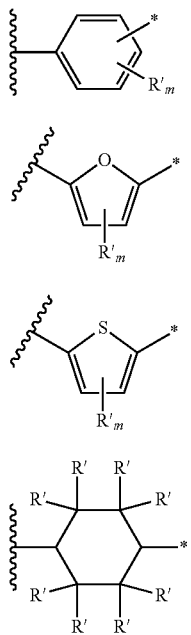

(L-10)

(L-11)

(L-12)

(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

5. An organic semiconductor material for a non-light-emitting organic semiconductor device, containing a compound represented by one of the following general formulae (2-3') and (2-4'):

General Formula (2-3')

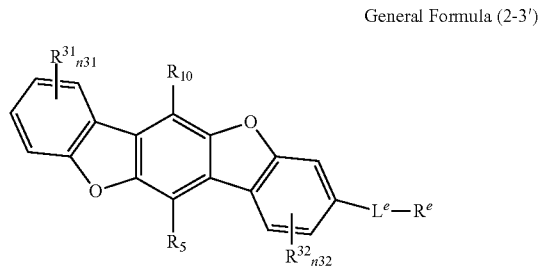

wherein in the general formula (2-3'), $L^e$ represents a divalent linking group represented by the following general formula (L-3'); $R^e$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the following general formula (W)); $R_5$ and $R_{10}$ each independently represent a hydrogen atom or a substituent; n31 represents an integer of from 0 to 4; and n32 represents an integer of from 0 to 3, General Formula (2-4')

wherein in the general formula (2-4'), $L^f$ represents a divalent linking group represented by the following general formula (L-3'); $R^f$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the following general formula (W)); $R_5$ and $R_{10}$ each independently represent a hydrogen atom or a substituent; n41 represents an integer of from 0 to 4; and n42 represents an integer of from 0 to 3:

(L-3')

wherein in the general formula (L-3'), a position shown by a wave line represents a bonding position to the benzobisbenzofuran skeleton; a position shown by * represents the bonding position to one of $R^e$ and $R^f$ adjacent to the general formula (L-3');

-L-R  General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

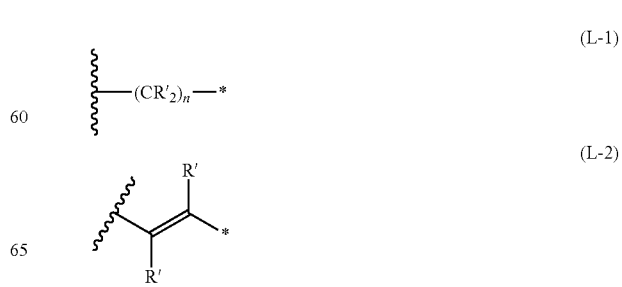

-continued

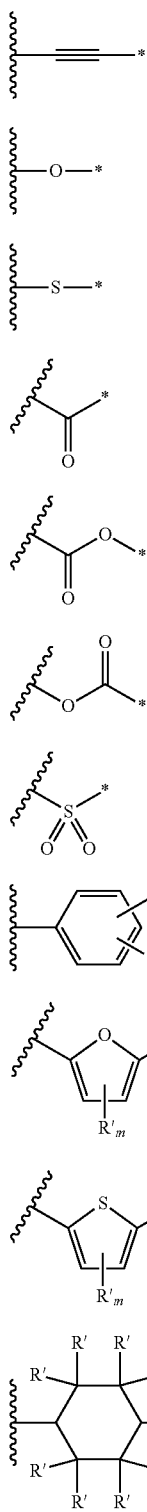

(L-3)
(L-4)
(L-5)
(L-6)
(L-7)
(L-8)
(L-9)
(L-10)
(L-11)
(L-12)
(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

6. A material for an organic thin film transistor, containing a compound represented by the following general formula (1):

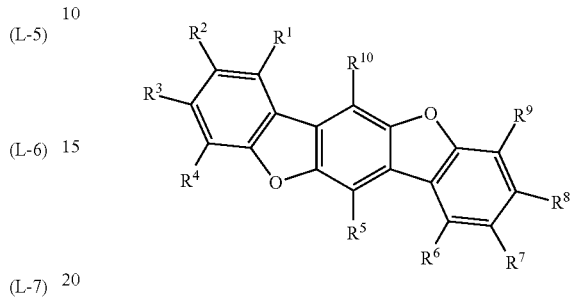

General Formula (1)

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R    General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

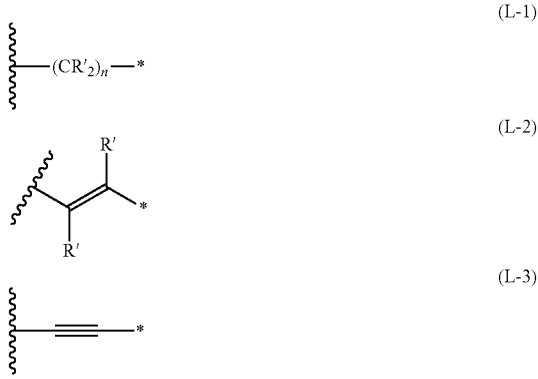

(L-1)
(L-2)
(L-3)

-continued (L-4)
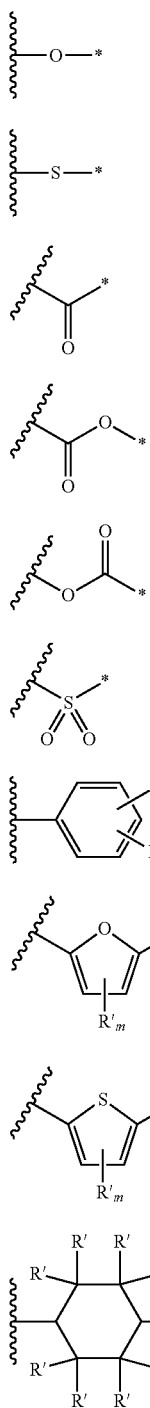

(L-5)

(L-6)

(L-7)

(L-8)

(L-9)

(L-10)

(L-11)

(L-12)

(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent, wherein the compound represented by the general formula (1) is a compound represented by one of the following general formulae (2-3) and (2-4):

General Formula (2-3)

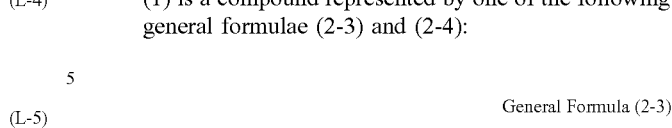

wherein in the general formula (2-3), $L^e$ represents a divalent linking group represented by the following general (L-3'); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the general formula (W)); $R_5$ and $R_{10}$ each independently represent a hydrogen atom or a substituent; n31 represents an integer of from 0 to 4; and n32 represents an integer of from 0 to 3, General Formula (2-4)

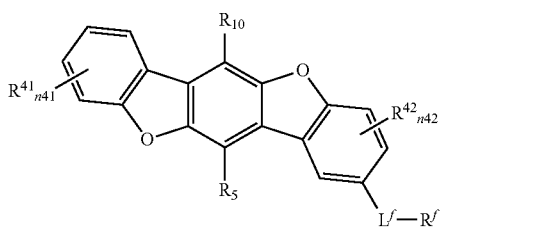

wherein in the general formula (2-4), $L^f$ represents a divalent linking group represented by the following general (L-3'); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the general formula (W)); $R_5$ and $R_{10}$ each independently represent a hydrogen atom or a substituent; n41 represents an integer of from 0 to 4; and n42 represents an integer of from 0 to 3:

(L-3')

wherein in the general (L-3') in the general formulae (2-3) and (2-4), a position shown by a wave line represents a bonding position to the benzobisbenzofuran skeleton; a position shown by * represents the bonding position to one of $R^e$ and $R^f$ adjacent to the general formula (L-3').

7. A coating solution for an organic thin film transistor, containing a compound represented by the following general formula (1):

General Formula (1)

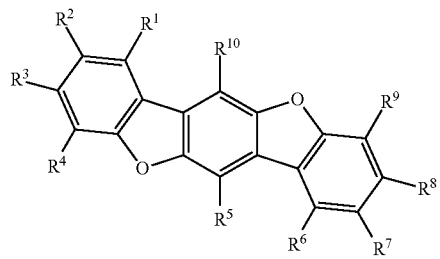

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R                General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

(L-1)
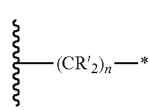

(L-2)
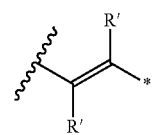

(L-3)
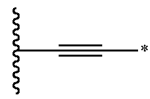

(L-4)
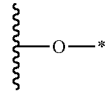

(L-5)
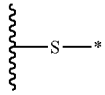

(L-6)
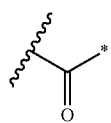

(L-7)
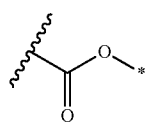

(L-8)
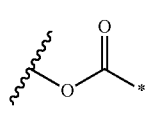

(L-9)
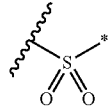

(L-10)
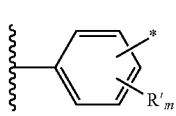

(L-11)
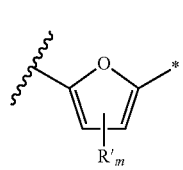

(L-12)
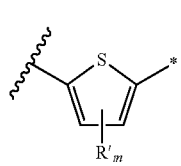

(L-13)
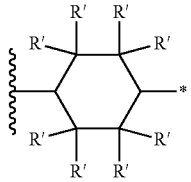

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent, wherein the compound represented by the general formula (1) is a compound represented by one of the following general formulae (2-3) and (2-4):

General Formula (2-3)

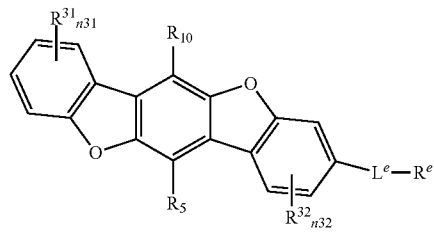

wherein in the general formula (2-3), $L^e$ represents a divalent linking group represented by the following general formula (L-3'); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the general formula (W)); $R_5$ and $R_{10}$ each independently represent a hydrogen atom or a substituent; n31 represents an integer of from 0 to 4; and n32 represents an integer of from 0 to 3, General Formula (2-4)

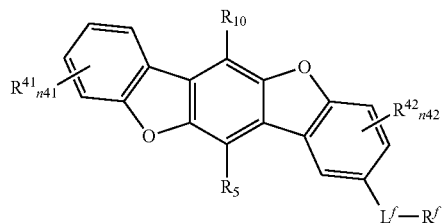

wherein in the general formula (2-4), $L^f$ represents a divalent linking group represented by the following general formula (L-3'); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the general formula (W)); $R_5$ and $R_{10}$ each independently represent a hydrogen atom or a substituent; n41 represents an integer of from 0 to 4; and n42 represents an integer of from 0 to 3:

(L-3')

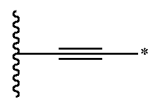

wherein in the general formula (L-3') in the general formulae (2-3) and (2-4), a position shown by a wave line represents a bonding position to the benzobisbenzofuran skeleton; a position shown by * represents the bonding position to one of $R^e$ and $R^f$ adjacent to the general formula (L-3').

8. A coating solution for an organic thin film transistor, containing a compound represented by the following general formula (1) and a polymer binder:

General Formula (1)

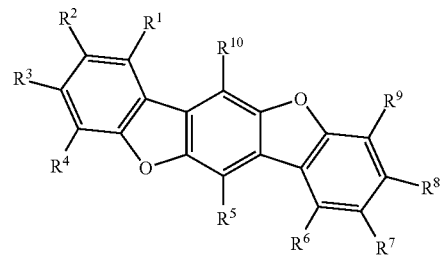

wherein in the general formula (1), $R^1$ to $R^{10}$ each independently represent a hydrogen atom or a substituent, provided that at least one of $R^1$ to $R^4$ and $R^6$ to $R^9$ represents a substituent represented by the following general formula (W), and in the in the general formula (W), when L represents a divalent linking group represented solely by the following general formula (L-1), at least two of $R^1$ to $R^4$ and $R^6$ to $R^9$ each represent a substituent represented by the following general formula (W), and the substituents represented by $R^1$ to $R^4$ and $R^6$ to $R^9$ do not form a condensed ring by being bonded to each other, -L-R     General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

(L-1)

(L-2)

(L-3)

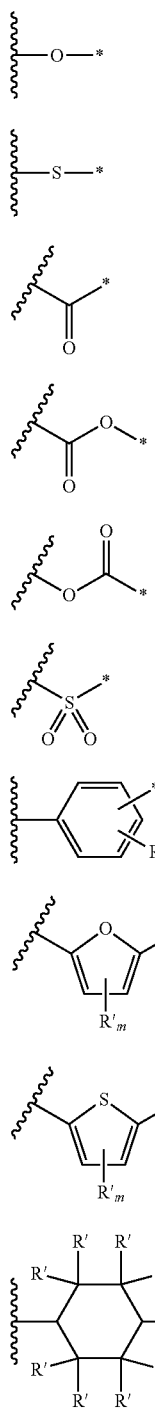

(L-4)
(L-5)
(L-6)
(L-7)
(L-8)
(L-9)
(L-10)
(L-11)
(L-12)
(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent, wherein the compound represented by the general formula (1) is a compound represented by one of the following general formulae (2-3) and (2-4):

General Formula (2-3)

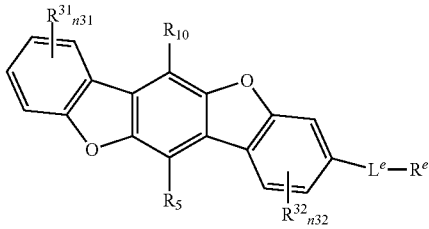

wherein in the general formula (2-3), $L^e$ represents a divalent linking group represented by the following general formula (L-3'); $R^e$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the general formula (W)); $R_5$ and $R_{10}$ each independently represent a hydrogen atom or a substituent; n31 represents an integer of from 0 to 4; and n32 represents an integer of from 0 to 3, General Formula (2-4)

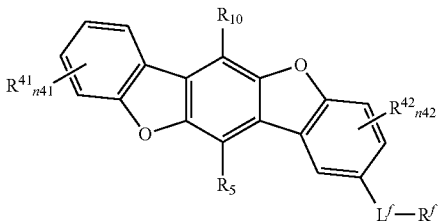

wherein in the general formula (2-4), $L^f$ represents a divalent linking group represented by the following general formula (L-3'); $R^f$ represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the general formula (W)); $R_5$ and $R_{10}$ each independently represent a hydrogen atom or a substituent; n41 represents an integer of from 0 to 4; and n42 represents an integer of from 0 to 3:

(L-3')

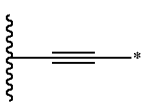

wherein in the general formula (L-3') in the general formulae (2-3) and (2-4), a position shown by a wave line represents a bonding position to the benzobisbenzofuran skeleton; a position shown by * represents the bonding position to one of $R^e$ and $R^f$ adjacent to the general formula (L-3').

9. An organic semiconductor thin film containing a compound represented by one of the following general formulae (2-3') and (2-4'):

General Formula (2-3')

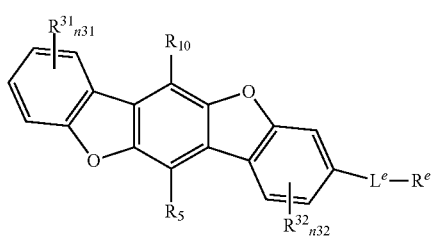

wherein in the general formula (2-3'), $L^e$ represents a divalent linking group represented by the following general formula (L-3'); $R^e$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{31}$ and $R^{32}$ each independently represent a substituent (provided that $R^{31}$ is not a group represented by the following general formula (W)); $R_5$ and $R_{10}$ each independently represent a hydrogen atom or a substituent; n31 represents an integer of from 0 to 4; and n32 represents an integer of from 0 to 3, General Formula (2-4')

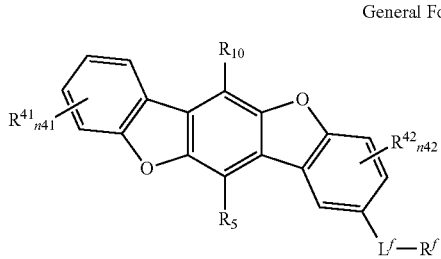

wherein in the general formula (2-4'), $L^f$ represents a divalent linking group represented by the following general formula (L-3'); $R^f$ represents a substituted or unsubstituted alkyl group having from 2 to 12 carbon atoms, an oligooxyethylene group having a number of repetition of oxyethylene units of 2 or more, an oligosiloxane group having 2 or more silicon atoms, or a substituted or unsubstituted trialkylsilyl group; $R^{41}$ and $R^{42}$ each independently represent a substituent (provided that $R^{41}$ and $R^{42}$ are not a group represented by the following general formula (W)); $R_5$ and $R_{10}$ each independently represent a hydrogen atom or a substituent; n41 represents an integer of from 0 to 4; and n42 represents an integer of from 0 to 3:

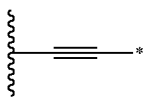
(L-3')

wherein in the general formula (L-3'), a position shown by a wave line represents a bonding position to the benzobisbenzofuran skeleton; a position shown by * represents the bonding position to one of $R^e$ and $R^f$ adjacent to the general formula (L-3');

-L-R  General Formula (W)

wherein in the general formula (W), L represents a divalent linking group represented by one of the following general formulae (L-1) to (L-13) or a divalent linking group containing two or more of divalent linking groups represented by any of the following general formulae (L-1) to (L-13) bonded to each other; and R represents a substituted or unsubstituted alkyl group having 2 or more carbon atoms, an oligooxyethylene group having a number of repetition of oxyethylene units of 2 or more, an oligosiloxane group having 2 or more silicon atoms, or a substituted or unsubstituted trialkylsilyl group, provided that R is capable of representing a substituted or unsubstituted trialkylsilyl group only in the case where L adjacent to R represents a divalent linking group represented by the following general formula (L-3):

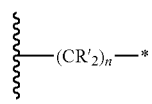
(L-1)

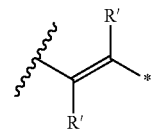
(L-2)

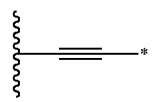
(L-3)

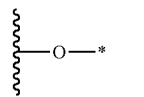
(L-4)

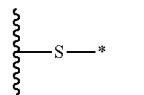
(L-5)

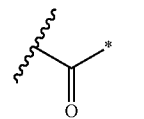
(L-6)

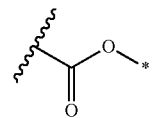
(L-7)

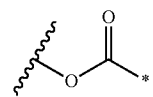
(L-8)

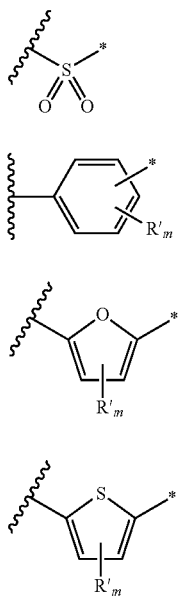
(L-9)

(L-10)

(L-11)

(L-12)

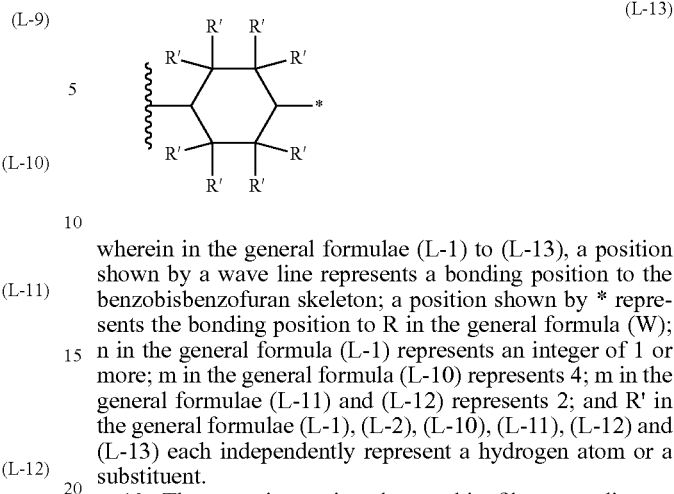
(L-13)

wherein in the general formulae (L-1) to (L-13), a position shown by a wave line represents a bonding position to the benzobisbenzofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11), (L-12) and (L-13) each independently represent a hydrogen atom or a substituent.

10. The organic semiconductor thin film according to claim 9 which further contains a polymer binder.

11. The organic semiconductor thin film according to claim 9, wherein the organic semiconductor thin film is produced by a solution coating method.

* * * * *